US010610684B2

(12) United States Patent
Kjeken et al.

(10) Patent No.: US 10,610,684 B2
(45) Date of Patent: Apr. 7, 2020

(54) VARIABLE CURRENT DENSITY SINGLE NEEDLE ELECTROPORATION SYSTEM AND METHOD

(75) Inventors: Rune Kjeken, Oslo (NO); Stephen Vincent Kemmerrer, San Diego, CA (US); Feng Lin, San Diego, CA (US); Dietmar Rabussay, Solana Beach, CA (US); Thomas Joseph Kardos, Aliso Viejo, CA (US)

(73) Assignee: Genetronics, Inc., San Diego, CA (US)

( * ) Notice: Subject to any disclaimer, the term of this patent is extended or adjusted under 35 U.S.C. 154(b) by 186 days.

(21) Appl. No.: 12/836,163

(22) Filed: Jul. 14, 2010

(65) Prior Publication Data

US 2011/0009807 A1 Jan. 13, 2011

Related U.S. Application Data

(63) Continuation of application No. PCT/US2009/000273, filed on Jan. 16, 2009.

(60) Provisional application No. 61/011,772, filed on Jan. 17, 2008.

(51) Int. Cl.
| | |
|---|---|
| *A61N 1/30* | (2006.01) |
| *A61N 1/32* | (2006.01) |
| *C12N 15/87* | (2006.01) |
| *C12M 1/42* | (2006.01) |
| *C12N 13/00* | (2006.01) |

(52) U.S. Cl.
CPC ............ *A61N 1/327* (2013.01); *C12M 35/02* (2013.01); *C12N 13/00* (2013.01); *C12N 15/87* (2013.01); *A61N 1/325* (2013.01)

(58) Field of Classification Search
CPC ........ A61N 1/327; A61N 1/325; A61N 1/306; A61N 1/0424; A61N 1/0476; A61N 1/30; A61M 5/32; A61M 5/46
USPC .......................................................... 604/21
See application file for complete search history.

(56) References Cited

U.S. PATENT DOCUMENTS

| | | | |
|---|---|---|---|
| 5,246,437 A | 9/1993 | Abela | |
| 5,300,029 A | 4/1994 | Denance | |
| 5,389,069 A | 2/1995 | Weaver | |
| 5,536,267 A * | 7/1996 | Edwards | ............ A61B 18/1477 604/22 |
| 5,702,359 A | 12/1997 | Hofmann | |
| 5,964,726 A | 10/1999 | Korenstein | |
| 6,314,316 B1 * | 11/2001 | Gilbert et al. | .................. 604/20 |
| 6,391,005 B1 | 5/2002 | Lum | |
| 6,519,492 B1 | 2/2003 | Yoo | |

(Continued)

FOREIGN PATENT DOCUMENTS

| | | |
|---|---|---|
| WO | WO 2005/094682 | 3/2005 |
| WO | WO2006084173 | 8/2006 |

*Primary Examiner* — Quynh-Nhu H. Vu
(74) *Attorney, Agent, or Firm* — BakerHostetler

(57) ABSTRACT

This invention comprises an improved electroporation electrode system comprising a single needle and a ring or donut shaped electrode wherein the difference in surface area of the electrodes provide for a substantial reduction of current density near the surface of the treated tissue and a more concentrated current density sufficient for electroporation only in tissues adjacent to the terminal portion of the single needle electrode. Thus, this invention provides for targeting specific tissue for electroporation and also should provide for lessening the sensation of electric current in the treated tissue.

26 Claims, 21 Drawing Sheets

(56) References Cited

U.S. PATENT DOCUMENTS

| | | | |
|---|---|---|---|
| 6,613,026 B1 * | 9/2003 | Palasis | A61B 17/32037 |
| | | | 106/264 |
| 6,635,027 B1 * | 10/2003 | Cragg | A61B 17/22 |
| | | | 604/22 |
| 6,697,669 B2 * | 2/2004 | Dev | A61N 1/0424 |
| | | | 604/21 |
| 6,706,016 B2 | 3/2004 | Cory | |
| 6,969,373 B2 * | 11/2005 | Schwartz | A61M 5/158 |
| | | | 604/152 |
| 6,981,971 B2 | 1/2006 | Caldera | |
| 7,404,815 B2 | 7/2008 | Kollias | |
| 2002/0058902 A1 * | 5/2002 | Kollias | A61N 1/303 |
| | | | 604/20 |
| 2002/0198512 A1 * | 12/2002 | Seward | 604/522 |
| 2005/0070841 A1 | 3/2005 | Mathiesen | |
| 2005/0154434 A1 * | 7/2005 | Simon et al. | 607/116 |
| 2006/0084938 A1 | 4/2006 | Zhang | |
| 2006/0269531 A1 | 11/2006 | Beebe | |
| 2008/0234655 A1 | 9/2008 | Mathiesen | |

\* cited by examiner

Fig. 4A
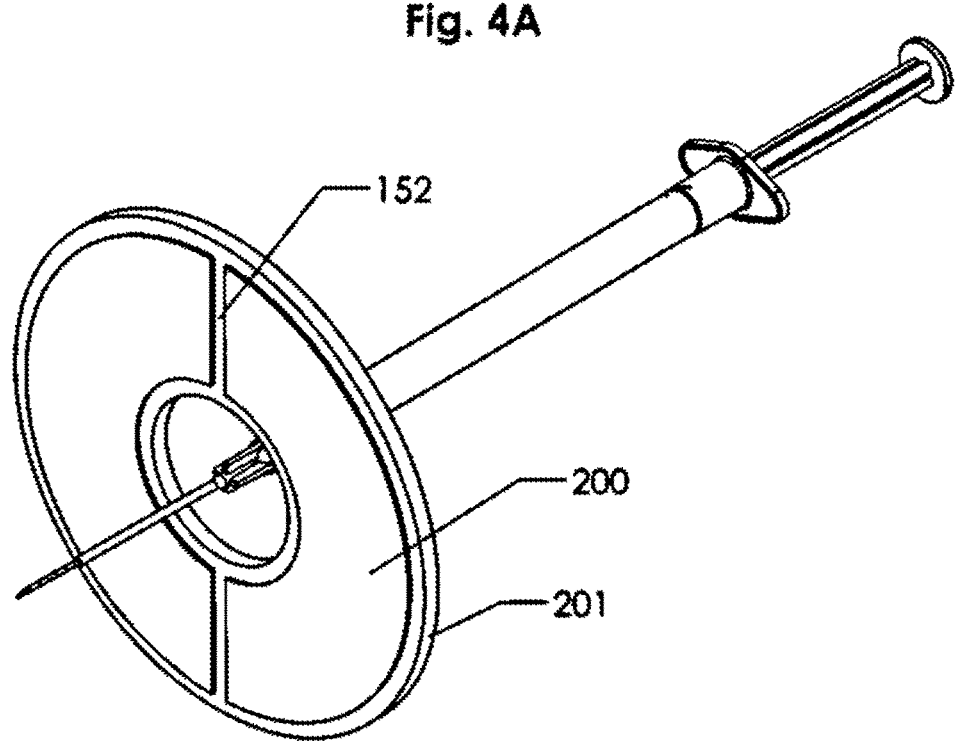
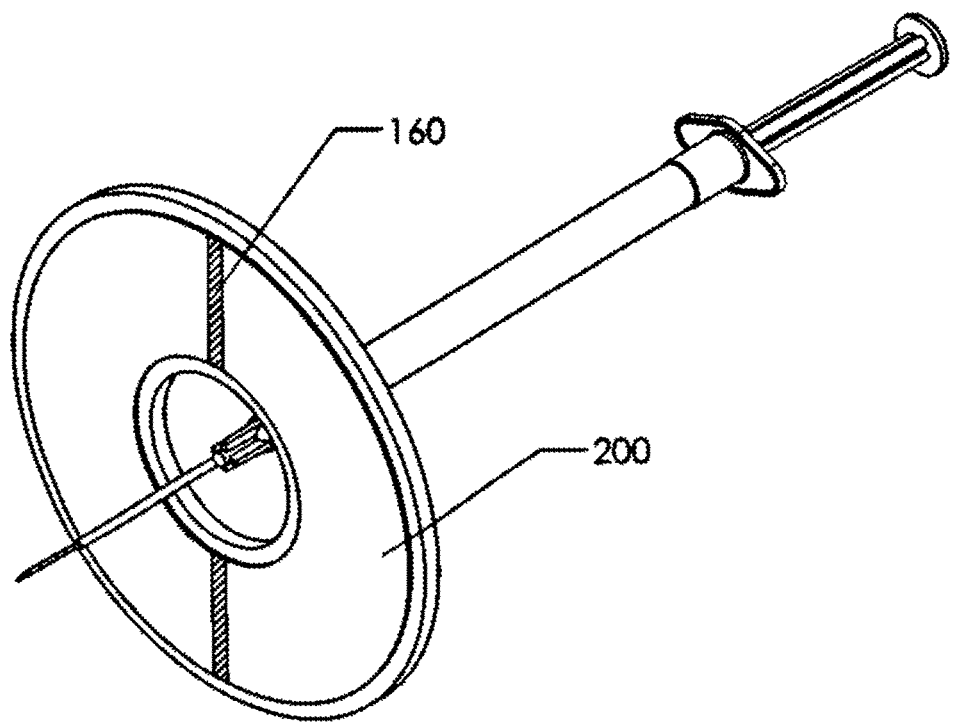
Fig.4B

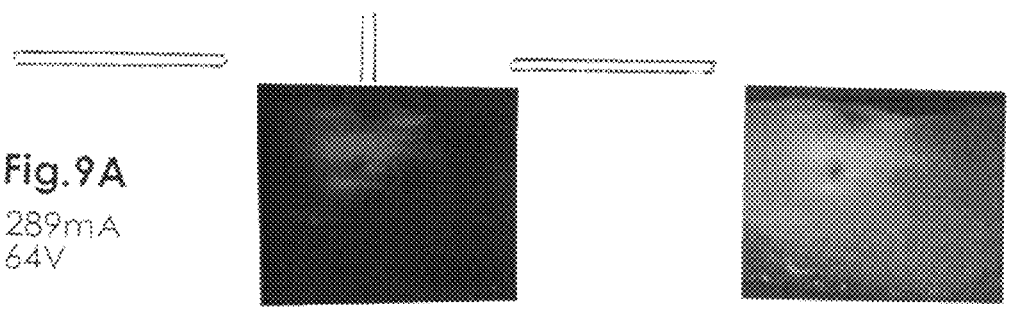
Fig.9A
289mA
64V
Fig.9B
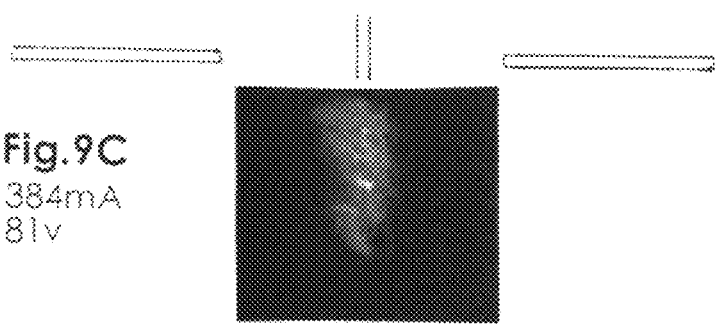
Fig.9C
384mA
81v
Fig.9D
579mA
103v
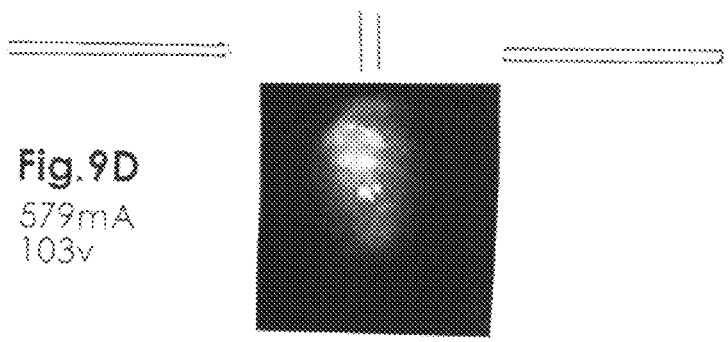
Fig.9E
758mA
138v
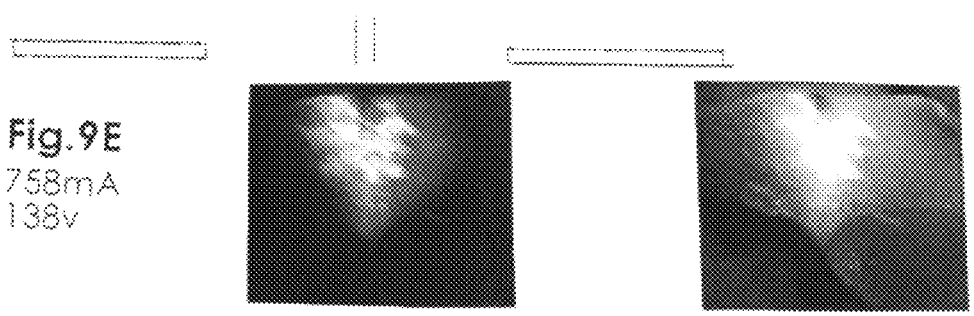
Fig.9F

189mA
58v

Section A-A

VARIABLE CURRENT DENSITY SINGLE NEEDLE ELECTROPORATION SYSTEM AND METHOD

FIELD OF THE INVENTION

The present invention relates generally to the use of electric pulses to increase the permeability of cells, and more specifically to methods and devices for applying controlled electroporative electric fields to in vivo tissues of humans and animals for the delivery of pharmaceutical compounds and nucleic acids into cells thereof. Further, this invention relates to an improved and novel electrode design for carrying out electroporation that provides for focused current density near the tissue treatment site undergoing electroporation and a simultaneous nonelectroporative electric field of decreased current density away from said tissue treatment site, which design provides for both focusing of electroporative electric pulses in a predetermined and measurable tissue volume, such as in skeletal muscle and/or dermal and subdermal tissues while providing additionally for a substantial reduction in electric current to nerve sensory cell-containing mammalian surface tissues.

BACKGROUND OF THE INVENTION

The following description includes information that may be useful in understanding the present invention. It is not an admission that any such information is prior art, or relevant, to the presently claimed inventions, or that any publication specifically or implicitly referenced is prior art.

The classical mode of administering vaccines and other pharmaceutical agents into the body tissues is by direct injection into muscle or skin tissues using a syringe and needle. As has been well disclosed in the art, incorporating electroporative pulses of electric energy with direct injection provides for delivery of such vaccines or agents directly into the cells within the tissue. Such direct delivery to cells using electroporative electric pulses can have a profound clinical effect on the quality of the response of the body's metabolic and/or immune systems over that of simple syringe and needle injection. Moreover, the capability of direct delivery of substances into the cell via electroporation has enabled the effective delivery of expressible naked DNA encoding a polypeptide, having any number of functions, including antigenic for eliciting of immune responses, or alternatively, metabolic for affecting various biologic pathways that result in a clinical effect.

Although electroporation technology allows for a more advanced delivery of substances to the cellular compartments in the body, the electroporative process, as presently commonly performed using tissue penetrating electrode arrays such as disclosed in U.S. Pat. Nos. 6,041,252, 6,278,895, and 7,245,963, has at least two distinct drawbacks for practical clinical use. These include first, the need to penetrate the skin barrier with multiple trauma inducing needles and second, no ability to easily determine the tissue volume undergoing electroporation. Classical electroporation technique, using arrays of spaced tissue-piercing needle electrodes provides for a relatively spread out area of tissue being electroporated. Typically, the tissue volume undergoing electroporation when using an array of spaced electrodes is larger than the volume bounded by the electrodes of the array. This is because of the natural flow of electric lines of force through the in vivo tissue between the positive and negative electrodes. How far around the outside of the array the elecroporative forces are capable of traveling is not easily quantifiable. This makes a quantifiable measure of the amount of drug being taken up by the cells very difficult. Thus, regarding control of therapeutic dose delivery, there remains a need to quantify the amount of tissue undergoing electroporation and consequently the dosage of drug being delivered into the cells of said tissue using electroporation.

With regard to tissue penetration, the typical spaced needle array design also causes substantial sensation of not only penetration of a multiplicity of needles into the flesh, but because of the exposed electrically conductive lengths of the penetrating electrodes the recipient of the electroporative pulse will experience a noticeable electric shock even if the upper portion of the inserted needle has a nonconductive coating. By upper portion here is meant that length of the needle that is in contact with surface and dermal tissues. Commonly, the electric pulse in the electroporation process is noticeable due to the fact that the pulse being sent between two exposed elongate electrodes sets up an electric field and an electric current through the entire depth of flesh penetrated by said electrodes. Since the skin tissues possess substantial nervous sensory cells, it is currently understood that the sensation of electric shock in the outer tissue regions is substantial. This typically unpleasant sensation is a drawback to the widespread acceptance and use of electroporation in such applications as vaccination. Further, assuming any sensation of electric shock is directly related to the tissue area or volume subject to the electric current of a certain strength, then it would reasonably appear, given that effective electroporation in a mammal is possible using only a single needle, as shown by the current inventors in co-pending patent application Ser. No. 11/894,653 herein incorporated by reference in its entirety, that use of spaced needle electrode arrays cause a far greater area of tissue to be subject to the electric pulse and consequent excitation of sensory nerve cells than is necessary. Thus, there is a need in the arts to find design configurations for delivering electroporative pulses while reducing the excitement of tissue surface and skin-based nerve cells.

Concerning the noticeable sensation of the electroporative pulse of electric energy, the level of sensation is also due in part to the design and typically bare metal nature of the electrodes used. For example, electrodes are typically constructed in various configurations such as, for example, calipers, meander electrodes, and noninvasive needle arrays for delivering an electric pulse to the surface of the skin, and underlying tissues close to the skin, and elongate and penetrating needle arrays for delivering electric pulses to deep tissue. Placement of electrodes directly onto the skin or piercing through it sets the electrode in areas of tissue where sensitivity to pain via nerve stimulation is very pronounced. Therefore, without a mechanism for lessening the current and current density in the areas of tissue having a high concentration of sensory nerve endings, the sensation of shock will likely remain.

Thus, there still exists a need in the art for electroporative methods, electrodes and systems that can provide for the ability to quantifiably measure the volume of tissue actually undergoing electroporation as well as provide for a substantial reduction in the electric energy directed in nerve sensory cell-containing tissues so as to provide for the possibility of reducing sensory cell excitement during the electroporation-assisted delivery of a therapeutic substance.

SUMMARY OF THE INVENTION

Turning now to the advantages of the present invention, disclosed is an apparatus for conducting the electroporation-assisted delivery to in vivo tissues of a mammal of therapeutic substances including expressible nucleic acid sequences encoding therapeutic polypeptides, or therapeutic forms of nucleic acids, or derivatives thereof. In a preferred embodiment the apparatus can be used to deliver directly to cells DNA sequences linked to a promoter and capable of expressing the polypeptide encoded thereby. In other alternate preferred embodiments, the apparatus can be used to deliver therapeutic substances comprising any of RNA, RNAi, siRNA, microRNA, and shRNA. Therapeutic substances can further include expressible nucleic acid sequences encoding cytokines, hormones and other functional molecules useful in therapeutic treatment of disorders and diseases.

The present invention also comprises an in vivo method, using pulsed electric fields to deliver therapeutic agents into cells of the skin, including dermal and underlying muscle compartments of the skin for local and systemic treatments. In a particularly preferred embodiment of the present invention, there is provided an in vivo method for introducing a therapeutic agent into body tissues and cells, such as cells within the dermis and muscle cells, particularly muscle cells in the dermis and skeletal muscle cells located in deeper tissue. Therapeutic agents contemplated for use with the invention method include naked or formulated nucleic acid, including RNAi, siRNA, microRNA, and shRNA, polypeptides and chemotherapeutic agents, and other therapeutic agents that can be employed directly as palliative agents (i.e., those which directly exert a therapeutic effect), or as agents with a less direct effect (e.g., genes encoding polypeptides that elicit an immune response).

In another embodiment, the apparatus of the invention provides for the capability of delivering to in vivo tissue an electroporative pulse of electric energy comprising a high current density at and near the tissue treatment site undergoing electroporation and, simultaneously, a nonelectroporative electric field having a correspondingly substantially lowered or diffused current density away from said tissue treatment site. Specifically, as disclosed herein, the invention apparatus comprises a single tissue penetrating needle electrode and a corresponding ring counter electrode, described further below, comprising a planar and generally circular or ovoid structure spatially situated with respect to the elongate electrode such that the elongate electrode is preferentially central and perpendicular to the planar ring electrode surface as shown in FIG. 2. The actual shape of the "ring" electrode can comprise variable geometries such as for example round, ovoid, triangular, square, rectangular, pentagonal, hexagonal, etc.

In another embodiment the single central elongate electrode has a tissue piercing distal end and proximate end mounted to a substrate. The elongate electrode can be solid or tubular, in which latter case said electrode is capable of delivering a fluid substance therethrough. In alternative embodiments the tubular configuration can comprise a fenestrated hypodermic needle (i.e., ports for expelling fluid substance are along the sides of the needle) or, in an alternate particularly preferred embodiment, the tubular electrode can comprise a fenestrated needle wherein there is no aperture at the tip of the tubular needle. In such an arrangement fluid media expressed through the tube will not expel out the tip of the needle but instead exclusively through the side ports. In a further embodiment the side ports are positioned on the elongate electrode along at least the electrically conducting distal 0.1 to 1.5 cm portion of the tube. In a related embodiment, the apertures forming the multiplicity of side ports provides the surprising capability of uniform distribution of the injected substance into the tissues intended to undergo electroporation where the diameter of said apertures are smaller than about 120 microns and present in number generally about between 10 and 100, preferably between 20 and 60 and even more preferably between 20 and 40 apertures per 1 cm length of electrode. This arrangement provides for the ability to easily apply a constant force/pressure on the fluid, such as animatedly by applying thumb pressure on a plunger on a syringe in fluid communication with the needle, and maintain approximately even distribution into the tissue along the entire length of the fenestrated part of the needle.

In still further related embodiments, the needle electrode is not placed in a static or fixed position with respect to the ring electrode. Rather, the elongate needle electrode can be attached to a reservoir such as a hypodermic syringe or the like, via the substrate at the electrode upper end, wherein the reservoir and needle electrode are movable in a plane perpendicular to the plane of the ring electrode surface such that the reservoir and electrode can be moved by an actuator mechanism so as to move the needle/reservoir from a first position to a second position relative to the ring electrode. The first position comprises a resting position wherein the electrode needle tip lies no further towards the plane of the ring electrode surface (i.e., the surface intended to contact the tissue) than the plane of the ring electrode. In such position, the needle does not contact the tissue. The second position comprises an extended position wherein the tip of the needle lies between 0.5 and 4.0 cm away from the plane of the ring electrode in the direction of the tissue which would therefore place the needle tip in a position between 0.5 and 4.0 cm into the tissue when the ring electrode is in contact with the tissue surface.

With respect to tubular electrode embodiments of the elongate needle electrode, the electrode is capable of passing flowable medium, such as injection substance, from a reservoir through the ports of the electrode (i.e., ports at the tip of the needle or alternatively fenestrated ports. The connection can be made by any number of methods such as for example where the substrate at the end of the electrode comprises a plastic hub and locking mechanism of a typical hypodermic needle. In a further embodiment, said elongate electrode has an electrically non-conducting surface along said electrode extending from the needle substrate mount to within between 2.5 and 0.1 cm from the needle distal end. In a further preferred embodiment, when said electrode is in contact with body tissues, electric current will not transmit from the electrode into the tissues along the section of the electrode having a non-conductive surface. In a further related embodiment the non-conductive surface can comprise any type of electrically inert substance. In a particularly preferred embodiment the material comprising the non-conductive surface can, as one of skill in the art will comprehend, be selected from any material that is biocompatible as well as nonconductive such as for example paralene, epoxy, rubber, plastic, Teflon™, and the like.

In accordance with the preferred embodiments of the present invention, the "ring" electrode comprises several useful attributes. In a first embodiment the electrode is generally of a ring- or ovoid shape, and an electrode surface area having a relatively uniform symmetry placement with respect to the central needle electrode. In a preferred embodiment, the ring electrode intended to be brought into contact with the skin has a surface area of at least about 2.5 $cm^2$ or more. In a further related embodiment, the surface area of the ring electrode is proportioned to the surface area of the electrically conductive portion of the elongate electrode so as to provide for substantial differences in current densities between said electrodes when an electric pulse is sent between the ring and elongate electrodes. Specifically, the current density at the elongate needle electrode surface ($I_E$) is related to the current density at the ring electrode surface $I_R$ described by the formula:

$$I_E/I_R = (A_R/A_E)$$

Where $I_E$ is the current density (Amps/cm$^2$) at the elongate electrode which is expressed as a ratio of surface Area of the ring electrode ($A_R$) over surface Area of the elongate electrode ($A_E$) and $I_R$ is the current density in Amps/cm$^2$ at the ring electrode. Thus, for example, if the current is 0.5 Amps, and surface area of the elongate electrode is 0.20 cm$^2$ and the surface area of the ring electrode is 20 cm$^2$, then the average current density at the surface of the ring electrode is 0.0125 Amps/cm$^2$ and the average current density at the needle electrode is 1.25 Amps/cm$^2$ during the duration of the electroporation pulse. The exposed surface area of the elongated electrode above is calculated for a 23 gauge needle with a nominal 0.64 mm diameter and a 1.0 cm un-insulated length as follows:

$$\text{Surface Area} = (\text{Length}) \times (\text{Circumference}) = (1 \text{ cm}) \times (2 \pi R) = (1 \text{ cm}) \times (2) \times (3.14159) \times (0.032 \text{ cm}) = 0.20 \text{ cm}^2$$

In a particularly preferred embodiment, the presence of said non-conductive surface on said elongate electrode provides for targeting or focusing of electric current of a density sufficient to cause electroporation of the cells in the vicinity of the distal portion of said elongate electrode. In such embodiment, electroporation of cells preferably takes place in areas surrounding said conductive portion of said electrode and extending into said tissue towards the ring electrode to a distance where a lowered current density is incapable of supporting sufficient electric energy to cause cell poration. In other words, the area of tissue undergoing electroporation is that area immediately surrounding the electrically conductive area on the elongate needle and into the tissue laterally and upward therefrom (i.e., towards the tissue surface) toward the ring electrode for a distance of at least between 0.0 and 0.5 cm depending upon the strength of the electroporative energy pulse. As the distance from said elongate electrode increases towards the ring electrode, the electrical field strength and the current density becomes too low to cause electroporation. In a particularly preferred embodiment, the sensation of electricity, which sensation thereof is related to the density of electric current, is likely greatly diminished at the tissue or skin surface due to the reduced current density. Further, given that cellular tissues such as skin and muscle tissues (i.e., epidermis, dermis, subdermis, muscle) possess an average conductivity, one can now determine experimentally the volume of the tissue subjected to an electric pulse having a sufficient field strength and current density to electroporate cells outward from the needle electrode into the tissue to a given distance. This advance allows for aligning drug volume/dose to be dispensed into a predetermined definable tissue volume with desired treatment outcome.

In another related embodiment, the ring electrode is designed as a "split" ring electrode that provides for the capability to monitor the proper placement of the electrode onto the skin surface prior to sending an electroporative pulse. Specifically, the ring is electrically isolatable in two or more parts, preferably in two electrically equal halves. This arrangement allows the electrode to be placed against the tissue surface and a sensory electric signal generated to sense the resistance between the surface of the electrode and the tissue surface. Once the sensor determines that the electrode is properly in contact with the tissue surface, as calculated by the relative resistances between each half of the electrode and tissue surface, the two halves of the ring electrode are brought into electrical communication with one another, the elongate needle electrode deployed into the tissue, and an electroporative pulse delivered to the in vivo tissue. This embodiment provides for ensuring that the effect of electric impedance of the tissue is uniform with respect to the ring electrode prior to delivering an electroporative pulse. In an alternate and/or simultaneous application with a split ring impedance sensor, the invention device can further include a pressure sensor associated with the ring electrode. In this embodiment the pressure sensor provides for determining a predetermined level of pressure the user must place with respect to the contact of the device onto the tissue surface of a subject before the apparatus will be pulsed. Sensing the pressure allows for the user of the device to tell when the device has been placed properly with respect to the tissue surface in order to maintain good electrical contact for an electroporative energy pulse.

In another embodiment, the invention apparatus can provide for manipulating the tissue surface to be drawn against the apparatus for making consistent contact with the tissue surface. In this embodiment, the apparatus can be equipped with a suction cup arrangement formed as a pliable diaphragm comprising the central section of the ring electrode. In this embodiment, the diaphragm is shaped as a suction cup as in a toy dart gun, the outer circumference in sealable connection with the inner circumference of the ring. Additional related embodiments provide for assisting in the generation of active suction of the cup which can include a spring activated pulling of the cup slightly outward from the plane of the ring electrode such that when the ring is pressed against a surface tissue, the tissue is urged upward into the cup recess. Following placement of the tissue in the cup recess, the elongate needle electrode can be driven through the suction cup diaphragm and into the tissue to the desired depth.

In yet another embodiment the invention apparatus provides for the sensing of the tissue type into which the elongate electrode is placed. In a preferred embodiment the invention device through its elongate electrode is equipped with a sensor capable of measuring the impedance of the tissue as the needle is inserted into said tissue. Thus, for example, as the electrode passes from one tissue type into another, such as for example adipose tissue to deep muscle tissue, the impedance sensed by the electrode changes thereby providing a direct indication that the electrode has passed from one type of tissue, e.g., adipose tissue, to another type, namely muscle.

In a particularly preferred related embodiment, the invention device is programmable for setting delivery of a fluid therapeutic substance through the side ports in the electrode at a predetermined position within a tissue type. Thus, for example, the device can deliver substances after the tip of the electrode has passed between 0.5 and 1.5 cm beyond, or deeper, than a tissue type interface, i.e., once the needle has passed beyond the adipose/muscle tissue interface, for example, the substance to be electroporated can be expelled into the muscle tissue. In a particularly preferred embodiment where the injectate is intended to be delivered to muscle tissue, fluid is not expelled until the tip of the elongate needle electrode has passed the adipose/muscle tissue interface and into the muscle tissue by between 0.5 and 1.5 cm. Alternatively, any depth of penetration can be programmed so that the specific delivery location in the tissue of substances can be predetermined. For example, it may be desirable, depending upon the indication, to deliver to dermal tissue, to adipose tissue, or to muscle tissue. Thus, it is another embodiment that the sensor can be used to indicate location of the penetrating needle for delivery of substances and electroporative pulses to any depth of tissue.

In still further embodiments, the invention device has a novel arrangement of electrical components such that the device is portable and can be used without attachment to a fixed source of electrical energy such as a wall outlet. In a preferred embodiment, the invention device possesses at least one capacitor having a nominal capacitance potential of 2000 uF (microFarads). In a further preferred embodiment the capacitor can be charged to a value of up to 200 Volts before sending energy discharges from said capacitor to the electrodes. In a particularly preferred embodiment, the circuitry is designed so as to relatively over-charge the capacitor and then, upon discharge of the capacitor, use a regulated voltage circuitry which allows for a constant voltage pulse or a relatively clean square wave pulse over the length of the pulse period to the patient even though the capacitor voltage drops due to dissipation of charge from the capacitor through the electrodes and treated tissue. Consequently, such arrangement allows for simulating a constant current pulse even though it is the voltage discharge that is regulated. By "regulated voltage" is meant a down-regulated voltage output during the pulse from the capacitor that is below the voltage at which the capacitor is charged, as shown in FIG. 6. Using such lower voltage allows for the pulse voltage to remain at a constant output during discharge of the capacitor. The voltage drop during the pulse (delta V) is approximated by the formula below where "i" is the current into the tissue being treated, "Q" is the charge on the capacitor having a maximum capacitance of "C", and t is the pulse length.

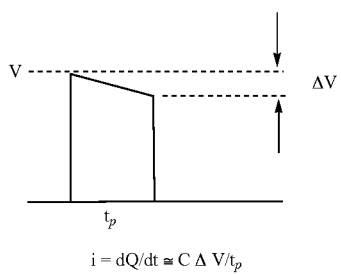

$$i = dQ/dt \cong C \, \Delta V / t_p$$

Thus, the regulated voltage output pulse is set below the maximum voltage V minus the expected drop ΔV across the pulse (or pulse train) so that each pulse is a relatively clean square wave thereby delivering a substantially constant voltage to the tissue. Since it has been determined that the tissue impedance seen between the elongate electrode and the ring electrode is fairly constant throughout the delivered pulse (particularly as for pulses intended for use in the electroporative delivery of therapeutic agents into cells), the substantially constant voltage will result in a substantially constant current into the tissue throughout the pulse length.

In yet further embodiments, the electrical circuitry allows for the capacitor to be charged either via a fixed electrical energy source such as an alternating current source directly or by induction, or by a battery-charging type unit.

In still another embodiment, the electric charge placed on the elongate electrode is the negative charged pole while the ring electrode is the positively charged pole. By negatively charged is meant electrons emit therefrom while by positive charged is meant that electrons are attracted thereto. This aspect provides the novel feature of providing for minimizing positive metal ion contamination into the body tissues from metal ions being generated from the positive electrode. As disclosed herein it has been found that ion shedding takes place almost exclusively at the positive pole. Specifically, metal is shed essentially only from the positive electrode during electroporation. Thus, the instant invention provides the capability of providing an electroporative electric pulse of energy into the body tissues while minimizing the contamination of the biologic environment with potentially toxic metallic ions. Although ions are capable of being shed from the ring electrode proportional to the strength of the current and length of the pulse, the metal ions shed at the skin surface should stay outside the skin barrier and the body's biologic environment.

In accordance with another embodiment of the present invention, there is provided a method for inducing an immune response in a subject, comprising applying a pulsed electric field to cells within body tissues, particularly dermal and/or muscle cells of the subject, substantially contemporaneously with the application of an immune response-inducing agent to said body tissues, such that the immune response-inducing agent is introduced into said cells thereby inducing in the subject an immune response.

In accordance with still another embodiment of the present invention, there is provided a method for the therapeutic application of electroporation to cells within certain tissues including such as muscle cells within the dermis and underlying skeletal muscle cells of a subject for introducing a metabolic or otherwise systemic effect to the recipient. For example, the methods contemplated include gene therapy treatments wherein a gene encoding an expressible cytokine or chemokine or hormone or other polypeptide that has a direct therapeutic effect is administered to a mammal.

Still another embodiment contemplates an electrode kit for use in conjunction with electroporation therapy, said kit having a ring electrode assembly, said assembly comprising a ring electrode and elongate central electrode, said assembly designed for connecting to a device for handling said ring and elongate electrode assembly and using it with a source of fluid injectate and an electric energy source.

In Still further embodiments, the device design of the current invention can be tailored for use in vaccinating or otherwise treating domestic herd/food source animals such as cattle, sheep, goats and horses. In this embodiment, the ring electrode is designed with a multiplicity of short electrically conductive projections thereon. Such projections provide both the required total surface area ratio with the needle electrode and allows for proper contact with the skin surface tissue, the projections allowing for the ring/surface electrode to penetrate the animal's fur, pelt, hair, or wool coat.

BRIEF DESCRIPTION OF THE FIGURES

FIGS. 4A and B are perspective drawings showing split ring electrode embodiments wherein a ring electrode is either physically split into two halves with a small air gap 152 therebetween (FIG. 4A) or that is physically split but connected by a non-conducting substrate 160. In these embodiments, each half of the ring is electronically isolatable from one another.

FIGS. 9A, B, C, D, E and F depict color green fluorescent protein (GFP) staining photographs superimposed against a representation of the placement of a 25 cc surface area ring, and a needle electrode showing that the actual focus of electroporative energy in the tissue as exhibited by the GFP staining corresponds to the theoretically expected result disclosed in FIG. 7 depending upon the field strength and corresponding current density of the pulse. In FIGS. 9A (GFP staining) and 9B (GFP and visible light field) are shown results in rabbit muscle tissue using a nominal 289 mAmp/64 volt pulse. FIG. 9C shows a nominal 384 mAmp/81 volt pulse wherein a greater tissue volume than in FIG. 9A has undergone an electroporation pulse. In FIG. 9D is shown GFP staining following a nominal 579 mAmp/103 volt pulse exhibiting an even greater tissue volume undergoing electroporation, and in FIGS. 9E (GFP staining) and 9F (GFP and visible light field) are shown GFP staining following a nominal 758 mAmp/138 volt pulse of still greater tissue volume electroporation.

In FIG. 14A, In FIG. 14B, In FIG. 14C.

FIG. 15A shows that the electrodes used for sensing in this configuration are on the injection needle. Specifically, electrode 400 is electrically isolated from the tip of the needle which acts as the return electrode 401.

In FIG. 17A, the tip of a typical syringe needle can be constructed wherein the tip section acts as one electrically conductive pole while a second electrically conductive pole is cased about the tip electrode with an insulative material therebetween. In FIG. 17C the depicted electrodes can have insulation so as to focus sensing to only the region the tip of the electrodes are driven past, while in FIG. 17D, the electrodes not only possess insulated portion but also fenestrated ports per the presently disclosed invention elements.

DETAILED DESCRIPTION OF THE INVENTION

Figure 1:
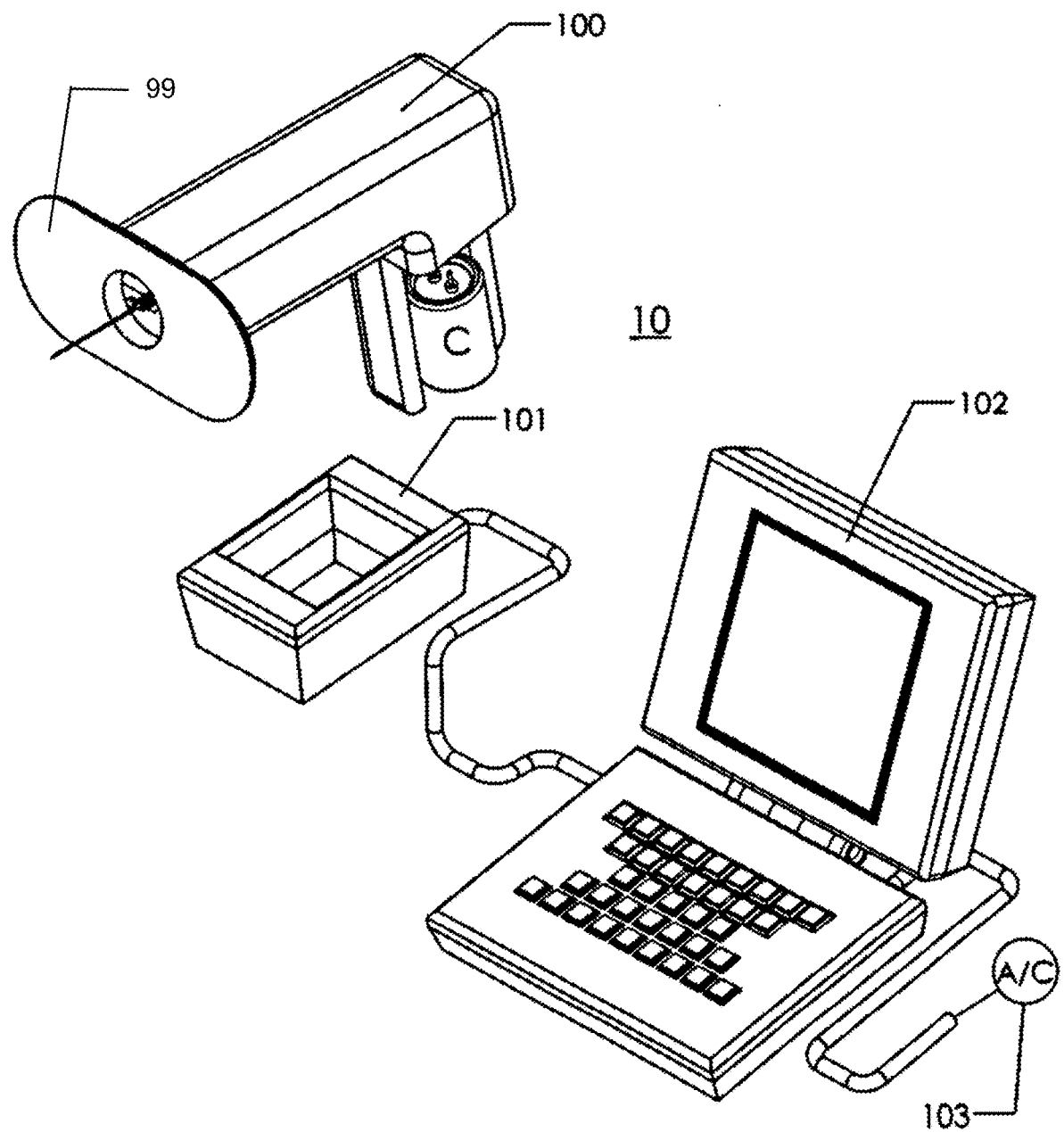
FIG. 1 shows a schematic drawing of an electroporation device system 10 comprising a ring-shaped electrode 99 (here the ring is depicted as ovoid in shape), a hand-held portable device 100 supporting the ring electrode and its assembly, a charging unit 101 for charging a capacitor (C) which is in electrical communication with said ring electrode assembly, a computer 102 operated software for setting pulse parameters and monitoring and recording pulsing conditions, and quality of charge imparted to said capacitor, which computer is powered by an external alternating current power source 103 or alternatively, a DC battery (not shown).

Turning now to further embodiments of the current invention, as used herein, "biocompatible" or "biocompatible material" means a material that is suitable for introduction into the human body for therapeutic purposes. For example, with respect to electrodes and materials such as insulation used for covering the electric conducting surfaces, such covering comprises materials that are inert and do not elicit irritation or allergy in the tissue of a mammal.

As used herein, "injection substance" means any injectable composition of a therapeutic agent to be delivered to a target tissue. As described herein, therapeutic agents comprising injection substances contemplated for use in the practice of the present invention include nucleic acids, polypeptides, chemotherapeutic agents and the like without limitation such as any nucleic acid disclosed throughout this letters patent as well as nucleic acid sequences encoding polypeptides such as for example, encoding IL-2, IL-12, ICAM-1, ICAM-2, ICAM-3, PSA, PSMA, PAP, MUC-1, Her-2, NS 3 and 4 etc., and nucleic acids comprising RNA, DNA, RNAi, siRNA, micro RNA, and shRNA. For purposes of this letters patent, injection substance can also include DNA coding for green fluorescing protein (GFP) and other substances used in visualizing location of materials injected into the tissue. Injection substances can further include pharmaceutical formulations comprising salts, excepients, and other materials for acceptable buffering as is will understood by those of skill in the pharmaceutical arts.

As used herein with respect to the application of an electroporative pulse of electric energy in tissue concomitant with an injection substance, the term "substantially contemporaneously" means that the electric pulse and the injection substance are delivered to the tissue reasonably close together in time. Preferably, the injection substance is administered prior to or concurrently with an electroporative pulse of electric energy. When applying multiple electrical pulses, the injection substance can be administered before or after each of the pulses, or at any time between the electrical pulses.

As used herein, the terms "impulse," "pulse," "electrical impulse," "electrical pulse," "electric pulse," "electropulse" and grammatical variations thereof are interchangeable and all refer to an electrical stimulus. Although the various terms are frequently used herein in the singular, the singular forms of the terms include multiple pulses. Preferred electrical impulses are pulsed electric fields applied for the purposes of reversible poration of cellular membranes. The pulse can be unipolar, bipolar, exponential or of a square wave or other form. Electric pulses contemplated for use in the practice of the present invention include those pulses of sufficient voltage, current, current density, and duration and frequency to cause electroporation in specified locations within a body tissue.

The Ring Electrode System

In a first embodiment, the invention device comprises an electrode system for performing electroporation of cells in vivo. In a preferred embodiment, the system comprises (1) a generally ring- or ovoid-shaped positive electrode, (2) an elongate tissue piercing single needle negative electrode comprising both a conductive and a non-conductive portion thereof, said single needle electrode positioned so as to lie along an axis central to said ring electrode and perpendicular to the plane of the ring electrode such that electric current can be directed to a limited electrode surface area on a distal portion of said needle electrode, (3) a mechanism for driving the single needle electrode into the tissue, (4) a mechanism for injecting a fluid containing an effective amount of a therapeutic agent through said elongate needle electrode, and (5) a source of electrical energy for charging a capacitor the discharge of which comprises at least one electric pulse, preferably a square wave regulated voltage pulse, for delivering an electroporative pulse of electric energy to the electrodes.

An example of the general embodiments of the current invention is shown in FIG. 1. Specifically, the system 10 includes a portable hand manipulateable housing 100 which is associated with the ring/needle electrode, a charging unit 101, a computer software system 102, and a source of electric power 103. This power source 103 can be A/C or D/C.

Figure 2:
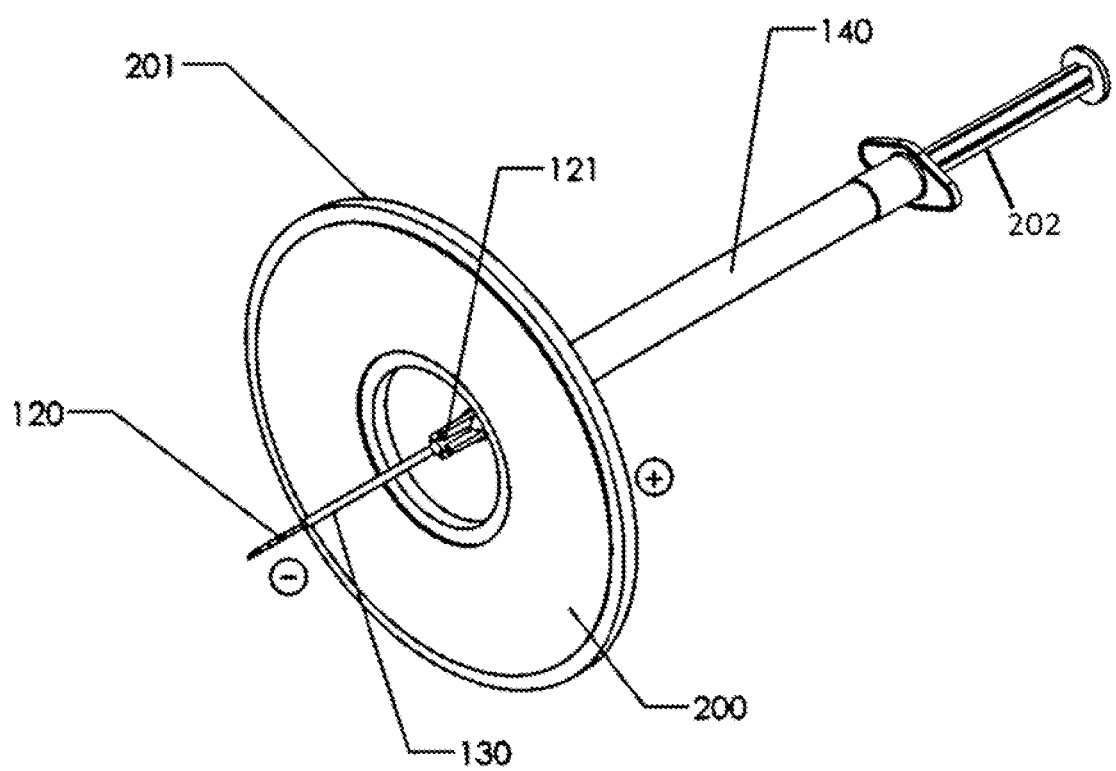
FIG. 2 is a perspective drawing of one example of the relative spatial arrangement between the elongate 120 and ring 200 electrodes. Specifically, the elongate electrode 120 is placed in a plane perpendicular with respect to the ring electrode 200 such that the elongate electrode 120 lies along an axis central to the ring electrode 200 and is in fluid communication with a reservoir 140. The elongate electrode 120 further comprises a section 130 that is nonconductive to electric current. The figure further depicts the substrate 121 comprising the proximal end of the elongate electrode as well as a support substrate 201 for supporting the ring electrode. The figure further depicts an actuator 202.

The housing element 100, further comprises drivers, which can be mechanically operated using cams, gears, and or levers, or by inanimate means such as an electric motor, for driving the single elongate electrode from a starting position to a terminal position, which movement of the electrode can be between a displacement of about between 0.5 and 4 cm. In a preferred embodiment, the single elongate electrode 120 (FIG. 2) acts also as an injection needle. Hence, at least a part of the injection needle 120 must be formed of a material possessing qualities of an electrical conductor. In a preferred embodiment, the driver manipulates the elongate needle by driving the reservoir itself which is attached to the needle. In a particularly preferred embodiment, the driver manipulates the body of a syringe such that the syringe is carried with the combination electrode/injection needle from the starting to the terminal positions.

Figure 3A:
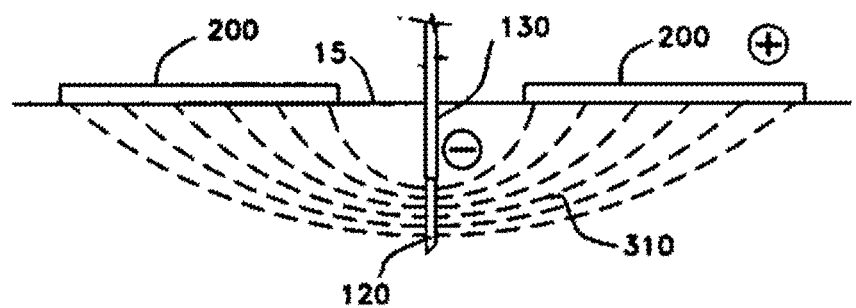
FIGS. 3A, B and C are related drawings showing in FIG. 3A a cross sectional representation of the ring and elongate electrode in tissue. Specifically, ring electrode 200 is shown engaged with tissue surface 15, with elongate electrode 120 having insulated section 130 in said tissue. Depicted are theoretical lines of force 310 due to a typical electroporative energy pulse that are concentrated to a higher current density at the elongate electrode 120 and less concentrated at the surface of the ring electrode 200.
Figure 3B:
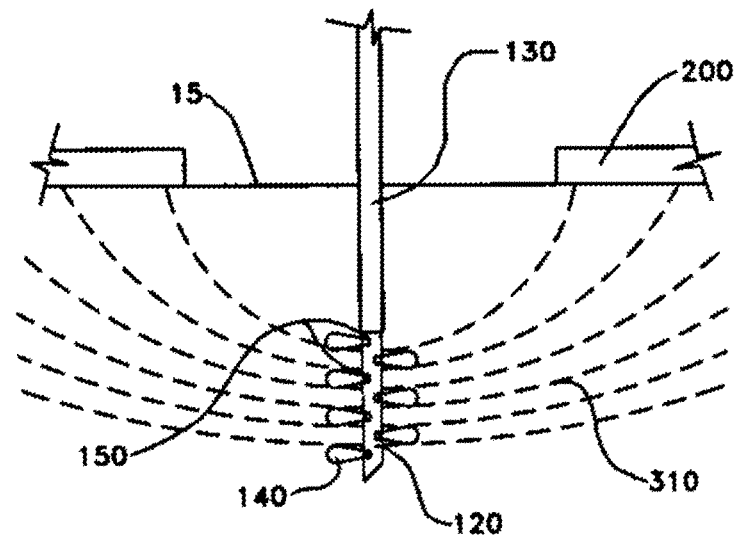
FIG. 3B depicts a close-up view of the elongate needle 120 with a multiplicity of bores 150 in the distal region of said needle 120. The figure further depicts ejectate 140 from said bores 150 and theoretical lines of electric force 310.
Figure 3C:
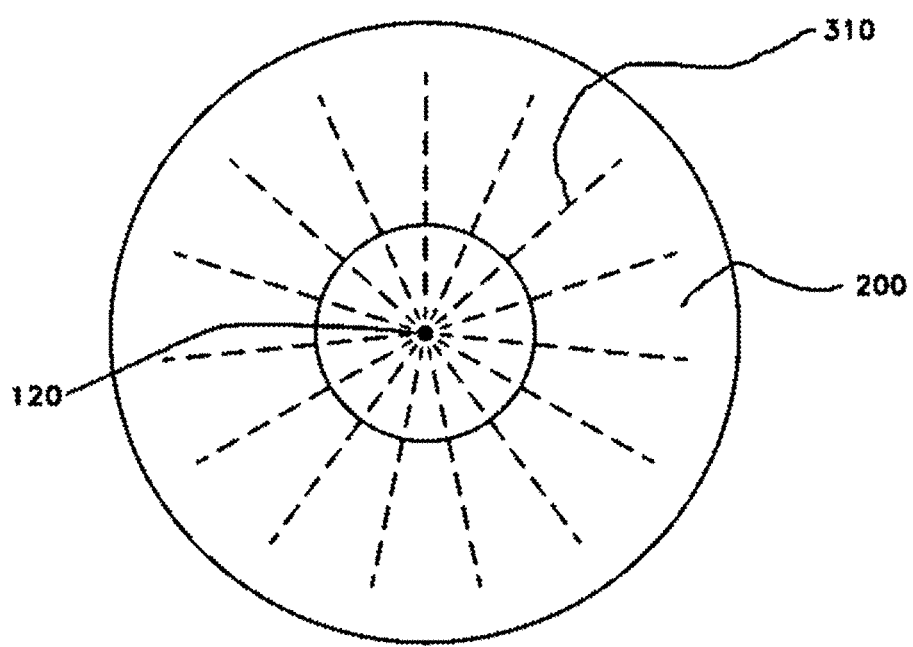
FIG. 3C is a top view depicting theoretical lines of electric force 310 radiating from central high current density needle electrode 120 to the low current density ring electrode 200.
Figure 5A:
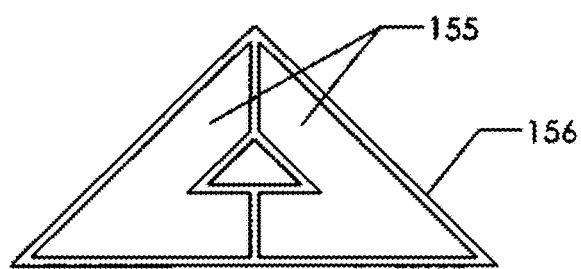
FIGS. 5A, B, C, and D are planar drawings depicting the electrode side 155 of split ring electrodes mounted in support substrate 156 for various useful shapes of a split ring electrode.
Figure 5B:
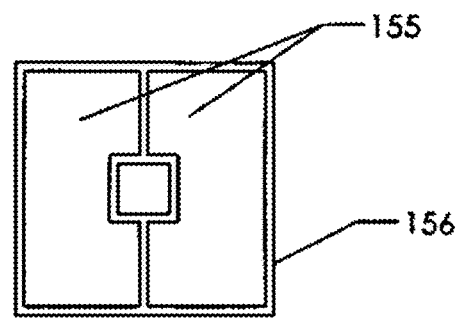
Figure 5C:
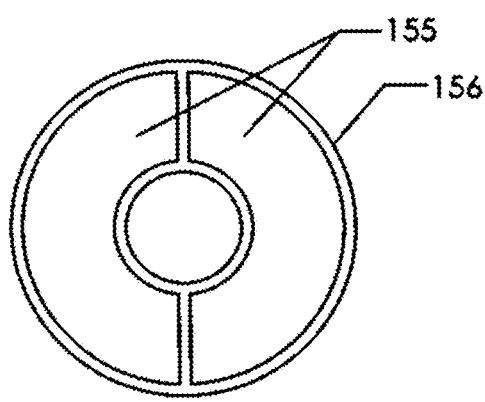
Figure 5D:
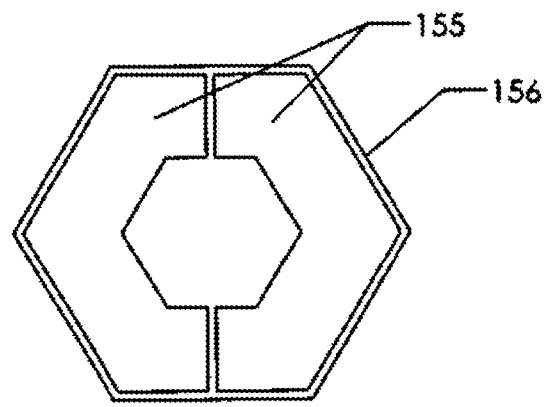
Figure 11A:
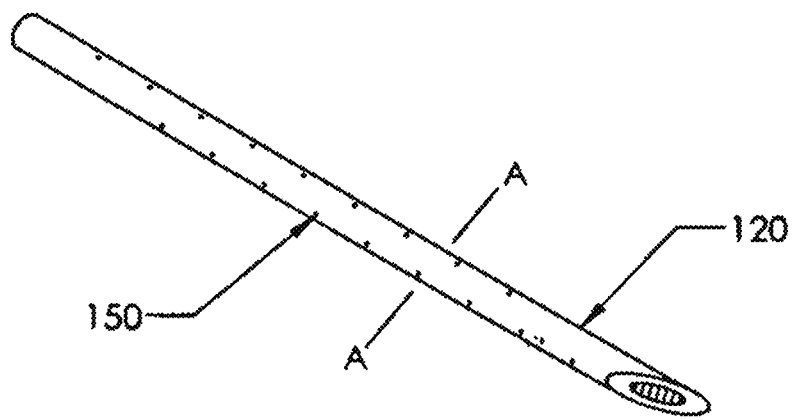
FIGS. 11A and B show schematic drawings depicting positioning of apertures along the electrically conductive portion of the elongate tubular electrode shaft. The apertures can be between 20 and 120 microns in diameter. As depicted, the apertures are spaced along the needle length (FIG. 11A) and at 90 degrees with respect to one another around the circumference of the needle shaft (FIG. 11B).
Figure 11B:
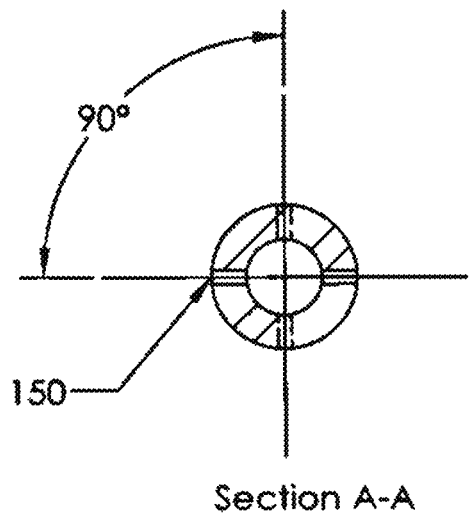
Figure 12:
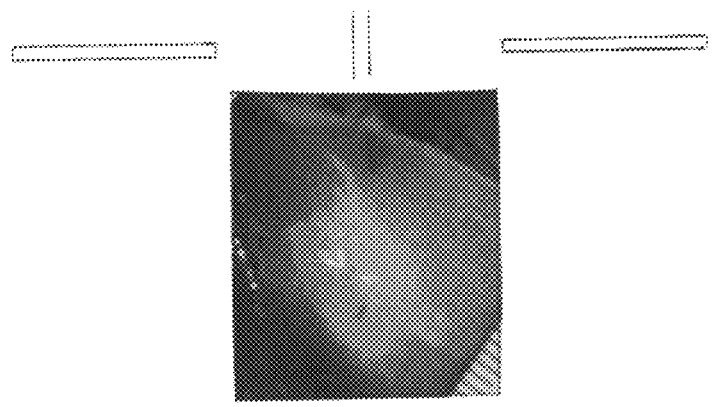
FIG. 12 is a color photograph showing a mixed fluorescent and visible light GFP staining in muscle tissue following dispersion of injection of the GFP through 60 micron apertures. As observed the distribution of injection substance is evenly dispersed about the needle track in the muscle tissue.

In particularly preferred embodiments, the needle electrode can be modified to provide for radial delivery of an injection substance, for example, by providing one or more apertures disposed along its length and proximal to the needle tip (i.e., a fenestrated needle), wherein said apertures are in fluid communication with the hollow interior of the injection needle. The needle 120 can be formed of a biocompatible metal such as stainless steel, gold, silver, etc. In a further preferred embodiment, the elongate electrode 120 can be designed so as to not have a port at the tip of the needle in contrast to typical syringe needles. In such embodiment, the ports (apertures) are located only around the electrically conductive portion of the electrode shaft so that fluid expelled therefrom is directed to tissue directly in the area intended for delivering an electroporative pulse of electric energy as depicted in FIG. 3B. In contrast to typical fenestrated needles (wherein ejected fluid flows predominantly out of the port located at the tip of the needle, if present, or alternatively through the upper or first side ports contacted by the expressed fluid along the needle path due to fluid dynamics as is well understood by those of skill in the hydrologic arts), the fenestrated needles of the current invention, due to the size range of the apertures and the elimination of a tip aperture, provide for even distribution of fluid through said apertures along the entire length of the needle having said ports using only nominal pressures for injecting the fluid injection substances. By nominal pressures is meant that the pressure required to expel fluid from electrodes having micron sized aperatures is only the pressure typically required during the injection of a substance through a standard hypodermic needle. This surprising finding is brought about by sizing the apertures along the needle shaft to a diameter in the micron range as well as including a multiplicity of such apertures ranging from between 10 and 100, more preferably between 20 and 60 and even more preferably between 20 and 40 such apertures per 1 cm length of electrically conductive needle/electrode. Preferably, the aperture diameter for obtaining even expression of fluid through each aperature is between 20 and 120 microns, more preferably between 30 and 100 microns, and even more preferably between 30 and 80 microns. Specific diameters include 20, 25, 30, 40, 50, 60, 70, 80, 90, and 100 microns and any incremental diameters therebetween. Numbers of apertures preferably are at least 20/cm, more preferably at least 30/cm and even more preferably at least 40/cm of electrically conductive electrode length. As depicted in FIGS. 11A and B, a multiplicity of micron sized apertures can be spaced along the needle shaft and for cylindrical distribution therefrom, as depicted in FIG. 11B, the apertures can be spaced around the needle circumference at 90 degree angles such that 4 apertures oppose one another as shown or can be spaced around the needle circumference at 60 degrees to obtain more apertures per needle length. Further still, the apertures can be formed in the needle shaft in a spiral configuration such that when, for example, a 60 degree cross sectional placement of the apertures is employed, the apertures are not in the same cross section of the needle but are staggered off of a cross sectional plane so that the formation of the apertures along the needle shaft are in a spiral format. As further disclosed in FIG. 12, results from a GFP experiment show consistent distribution about the needle track of the expressed material as indicated by the cylindrical localization of the GFP. In this experiment the transfected volume was measured at 1.2 $cm^3$, the tissue having been subjected to two successive 6o millisec 98 V, 768 mAmp pulses delivered 200 millisec apart.

In still other embodiments, the single needle electrode has an insulated portion 130 that is not electrically conducting. In a particularly preferred embodiment, the non-conductive portion can be provided either by an insulation coating such as a biocompatible plastic, paralene, Teflon™, epoxy or other material that will not allow current to pass. Still further, the non-conducting portion of said elongate electrode is located on said electrode along its proximal region. Specifically, the elongate electrode will have a nonconductive surface between the proximal end, (which is in fluid communication with a reservoir containing an injection substance for delivery to body tissues) and terminating between 0.1 cm and 2.5 cm from the distal end of the electrode.

In a further embodiment, the ring-shaped electrode 200 may be formed in any planar shape having symmetry, including but not limited to, a circular ring, a donut circle, an oval donut, a rectangular ring, isosceles triangle donut, an equilateral triangle donut, a square ring donut, a rectangular donut, a pentagonal ring donut, and hexagonal ring donut or the like as shown, for example, in FIGS. 5A-D as long as the electrode is formed in a plane, is generally symmetrical (i.e., has a form that can be recognized as having a shape that is evenly divisible into two relatively equal electrically conductive portions), and is conductive at least on one side of the plane (i.e., the side facing the body surface against which the electrode is placed), the electrode further having an area central with respect to the ring structure that is empty of electrically conductive material such as a void or hole or alternatively a nonconductive material such as, for example, a pliable material such as rubber or silicon. Where such pliable material is present, such material can further be designed to act as a suction cup for urging surface tissue to be pulled outward from the tissue surface. In further embodiments the empty or nonconductive area forming the center of the ring allows for the elongate electrode to pass therethrough, whether through a void and directly into contact with a surface tissue or alternatively, through said resilient suction cup material and then into contact with said tissue.

In another attribute, the ring electrode is designed so that it can be electrically isolateable into two halves. Specifically, the ring can be manufactured either as two separate halves or can comprise two halves connected together by a non-conducting substrate (See FIGS. 4A and B). In this aspect, the ring electrode halves can be electrically isolated from one another which electrical arrangement provides for the capability of using the electrode to monitor quality of electrical contact of the ring electrode with the tissue surface. Specific electrical arrangements for carrying out sensing contact is easily understandable by one of ordinary skill in the electrical arts. In operation, for example, the ring electrode of the invention apparatus is pressed against the skin. The ring electrode system circuitry includes electric leads to each half of the split ring and an impedance check can be made for each half regarding the detected current or alternatively, resistance, measured between the electrode and surface tissue upon sending a nominal electric signal through each electrode half. If the ring electrode is properly placed against the tissue surface the resistance or current measured in each half will be essentially the same indicating that the user has applied the ring electrode and device to the tissue surface evenly so that when the single elongate electrode is driven into the tissue and the electric pulse sent between the elongate and ring electrodes, the current flow between the elongate and two halves of the split ring with be equivalent. Numerous split ring electrode shapes can be used including, for example, shapes depicted in FIGS. 5A-D.

With respect to embodiments wherein the void area in the center of the ring electrode comprises a rubber or other pliable nonconductive material for acting as a suction cup, the tissue surface can be urged into the cup by a suction mechanism causing the tissue to be drawn up against the resilient material thereby providing for additional close and consistent contact of the tissue with the electrode to support consistent electrical conductivity between the tissue surfaces and the ring electrode. The drawing up of the tissue against the suction cup further provides for maintaining a consistency in the depth of delivery of injection substances as between different treated subjects. When the tissue is drawn up against the suction, the elongate needle can be driven through the suction cup rubber and into the tissue to a consistent predetermined depth.

Figure 8:
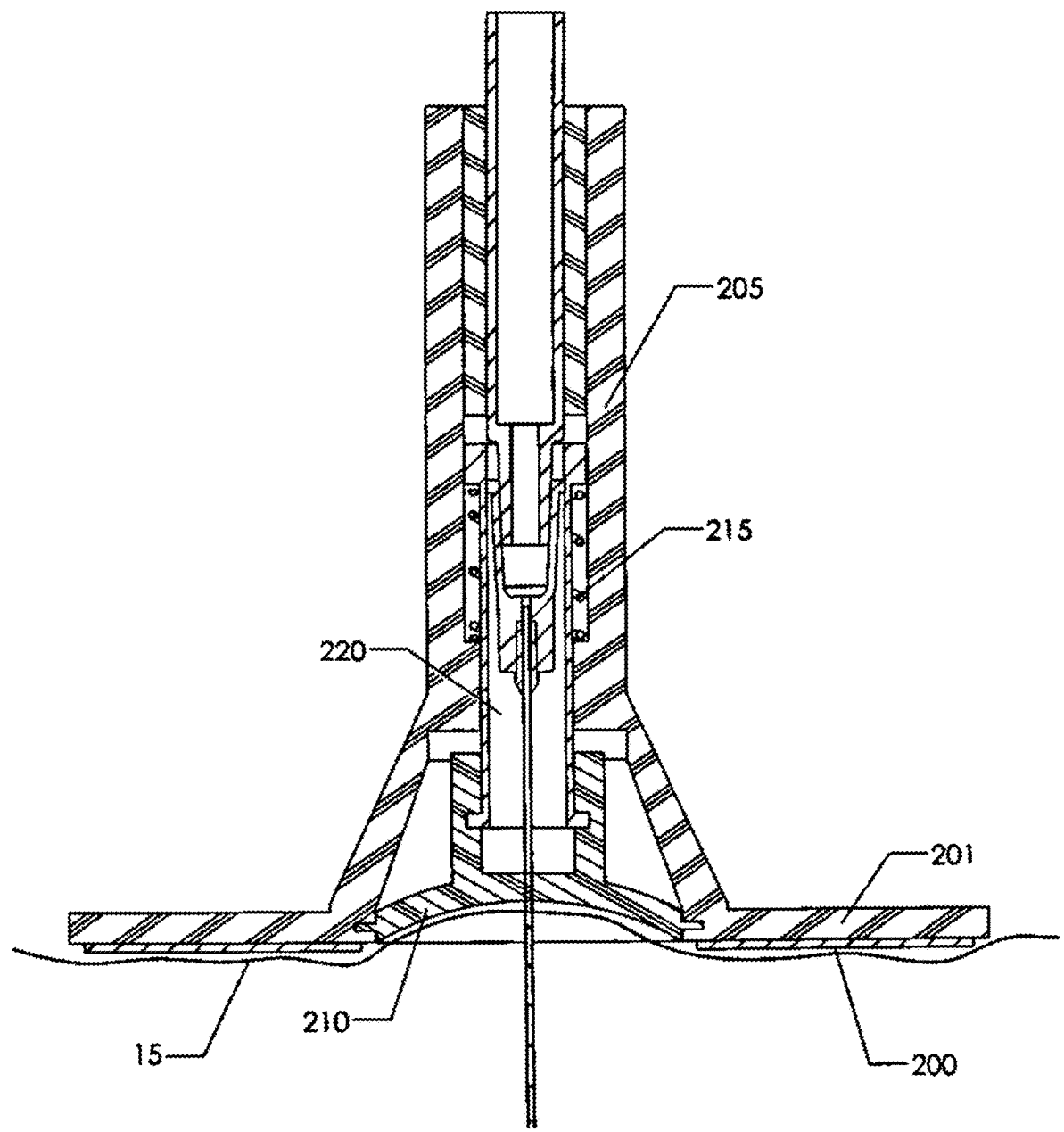
FIG. 8 is a cross-sectional drawing of the ring electrode support 201 covering the ring electrode 200 with centrally located pliable suction cup 210. As depicted, the suction cup 210 in this embodiment is connected to spring 215 assisted riser substrate 220 in slidable relation to a portion of either the assembly housing 205.

As shown in FIG. 8, for example, a mechanism can be incorporated into the ring electrode assembly comprising the resilient suction cup 210 in sealable connection with the ring electrode substrate 201. Specifically, for example, a spring 215 loaded riser substrate 220 in slideable relation to the assembly housing substrate 205 can be connected to the ring electrode for aiding the outward (from the tissue surface) pull of the suction cup which in use will provide for urging the surface tissue outward.

In a preferred embodiment the elongate electrode is in fluid communication at its proximate end to a reservoir containing an injection substance. In a further preferred embodiment, the invention apparatus includes a driver mechanism for driving the elongate electrode and optionally said reservoir attached thereto from a starting position to a terminal position in relation to said housing and ring electrode. Preferably, the length of travel of the actuated elongate electrode can be anywhere between 0.5 and 4 cm. For embodiments comprising a suction cup, the needle is directed to pierce through the suction cup and into the tissue.

In still another concomitant and/or alternate embodiment, the ring electrode system can comprise a pressure sensor associated with the ring electrode as one of skill in the electrical and mechanical arts will understand how to make. In this embodiment a pressure sensor is arranged such that when the ring electrode is pressed against the tissue surface, the sensor will measure the physical pressure applied to the device against said tissue. If the value of pressure is sufficient, the device will be capable of activating the sending of an electroporative pulse of electric energy to the electrodes. In preferred embodiments the requisite pressure for activation of the device can be between 0.5 and 1 lbs/sq inch. As one of skill in the respective arts will understand, the invention apparatus includes software for measuring said pressure for determining the amount of physical force placed on the ring electrode against the tissue surface. It should be understood that the application of such physical force is intended to assist good electrical contact between the ring electrode and tissue surface. For embodiments comprising a suction cup, such pressure also assists the function of the suction cup so that when the suction is activated, the tissue will be easily drawn against said suction cup.

In still further embodiments, the current invention provides for a heretofore not discovered capability of avoiding the shedding of potentially toxic metal ions into the tissues of a mammal when using standard stainless steel tissue penetrating electrodes. Whereas it is known that use of gold-coated stainless steel electrodes will provide non-shedding of toxic heavy metals present in stainless steel into the tissues as disclosed in U.S. patent application Ser. No. 10/516,757, use of gold is not as desired as stainless steel because of the added cost of the gold as well as the application of gold to an electrode. Surprisingly, as here in disclosed, stainless steel can be used in tissue penetrating electrodes where, as in the instant case, there is but a single tissue penetrating electrode and a corresponding counter electrode that is non-tissue penetrating. In this instance the stainless steel penetrating electrode will shed minimal amounts of metallic ions into the tissue if such electrode acts as the negatively charged electrode while the non-tissue penetrating electrode, such as the herein disclosed ring electrode, acts as the positive electrode.

In experiments by the current inventors, standard stainless steel hypodermic injection needles, set as either the negative or positive electrode, were tested against a gold electrode, also set as either the negative or positive electrode, in physiologic saline. Where the gold electrode was set as the negative and the stainless steel electrode set as the positive, metallic ions found in the solution following two 60 millisecond electroporation pulses of a 400 mAmp current and 40 Volts were as follows: Manganese 0.035 ppm (parts per million), Nickel 0.200 ppm, Molybdenum less than 0.003 ppm, Chromium 0.413 ppm, and Iron 0.977 ppm. In contrast, when the gold electrode was set as the positive and the stainless steel electrode set as the negative under the same conditions there was virtually no detectable metallic ions shed into solution, i.e., in each case, whether Manganese, Nickel, Molybdenum, Chromium, or Iron, less than 0.003 ppm were observed.

In a particularly preferred embodiment, the surface area of the ring electrode is proportional to the surface area of the elongate electrode. Generally, the ratio of the ring electrode surface area to the surface area of the needle electrode is at least 5:1, respectively. Preferably, the ratio of the surface areas of the ring to the elongate electrode is between 10:1 to 1000:1. Ratios of 10:1 are preferable for use in human subjects while a ratio between 5:1 and 10:1 is acceptable for use in herd animals. In related embodiments the ring electrode can have a surface area of between 1 $cm^2$ and 100 $cm^2$ and the electrically conductive portion of the elongate electrode can have a length of between 0.01 cm and 3.0 cm. For elongate electrodes having such a linear dimension range the surface areas corresponding to such lengths depend upon the gage of the electrodes (i.e., their respective outer diameters). As shown in the following Schedule A elongate electrode surface areas are as delineated using the formula: Area=CL=$\pi$DL to calculate where D is diameter and L is exposed length:

Schedule A

| Needle Gauge | Dia (mm) | Conductive Length (cm) | | | | | |
|---|---|---|---|---|---|---|---|
| | | 0.5 | 1.0 | 1.5 | 2.0 | 2.5 | 3.0 |
| 20 | 0.91 | 0.14 | 0.29 | 0.43 | 0.57 | 0.71 | 0.86 |
| 21 | 0.82 | 0.13 | 0.26 | 0.39 | 0.52 | 0.64 | 0.77 |
| 22 | 0.72 | 0.11 | 0.23 | 0.34 | 0.45 | 0.57 | 0.68 |
| 23 | 0.64 | 0.10 | 0.20 | 0.30 | 0.40 | 0.50 | 0.60 |
| 24 | 0.57 | 0.09 | 0.18 | 0.27 | 0.36 | 0.45 | 0.54 |
| 25 | 0.51 | 0.08 | 0.16 | 0.24 | 0.32 | 0.40 | 0.48 |
| 26 | 0.46 | 0.07 | 0.14 | 0.22 | 0.29 | 0.36 | 0.43 |
| 27 | 0.41 | 0.06 | 0.13 | 0.19 | 0.26 | 0.32 | 0.39 |
| 28 | 0.36 | 0.06 | 0.11 | 0.17 | 0.23 | 0.28 | 0.34 |

Bold numbers in table are area in $cm^2$

In some embodiments, the needle electrode has an electrically conductive surface area between 0.05 and 1.00 $cm^2$. With respect to the above list of useful elongate electrode surface areas, in a particularly preferred embodiment the gauge of the electrode needle can be between 22 and 24 gauge ranging from about 0.1 to 0.6 $cm^2$ for up to an insertion depth of up to 4.0 cm.

With regard to the above ring and elongate electrode surface area ratios, such ratios correlate to current density wherein the relationship between the ring and elongate electrodes is described by the following formula as previously noted:

$$A_R/A_E = I_E/I_R$$

where $A_R$ is the surface area of the ring electrode, $A_E$ is the surface area of the elongate electrode, $I_E$ is the average current density at the elongate electrode, and $I_R$ is the average current density at the ring electrode. Thus, for any given surface areas of the elongate and ring electrodes, the ratios are directly proportional to the current density observable at the elongate and ring electrode surfaces. In a particularly preferred embodiment, the ratio of average current density of the ring electrode to the exposed elongated electrode is intended to have a value of anywhere from 1000:1 to 50:1, more preferably between 200:1 to 100:1. Further, such value ratios are directly associated with obtaining electroporative electric energies near the elongate electrode while obtaining nonelecroporative electric energies closer to the ring electrode. Such ratios further provide for a lessened current available to excit sensory nerve cells and thus provide for potential lessening of sensation of electric shock in the surface tissues near the ring electrode. This is particularly the case when delivering pulses of electric energy having a nominal current of between 0.01 Amp and 1.0 Amp (of constant current discharge pulse).

As is understandable to one of skill in the art, the difference in surface area of the elongate and ring electrodes provides for a condition while pulsing where electric current density is non-uniform throughout the volume of tissue lying between the electrodes. Specifically, current density is very high at the non-insulated portion of the elongate electrode (at least high enough to provide for electroporation of cells adjacent or near the electrode) and substantially lower at the ring-electrode surface as depicted in FIGS. 3A, B and C. In a particularly preferred embodiment, where the ring electrode assembly is designed with its symmetry imbued ring electrode at one end and the conductive portion of the elongate electrode at the other end, the current established in the tissue at any given distance between the ring and elongate electrode in a given plane perpendicular to the elongate electrode will, largely due to the symmetrical shape of the ring electrode, have the same current density. Further, the current density decreases relatively evenly in the tissue at each incremental measure towards the ring electrode. Thus, essentially all of the tissue in a given plane in the tissue around and extending into the tissue from the elongate electrode will experience the same lower current density than the density at the elongate electrode. Further still, the area of tissue intended to undergo electroporation is that tissue along the needle track in the conductive region of the elongate electrode and extending into the tissue to a distance therefrom sufficient to become electroporated (i.e., at least some of the cells lying between at least 0 and 0.5 cm from the needle track along that portion of electrode that is not insulated are subject to electroporation depending on the local field strength). The distance into the tissue from the needle track where electroporation will occur is dependent upon the pulse energy used as well as other factors. The higher the field strength of the pulse the farther into the tissue towards the ring electrode will be the threshold point for electroporation to occur.

Regarding the phenomenon of field strength as it relates to electroporation of intact tissues in the present invention, a way to visualize "Current Density" as it relates to "Field Strength" is as follows. For the theoretical condition of two parallel plates of area 1 cm$^2$ and a 100 volt potential across them, and further separated by a length L=1 cm, as shown below;

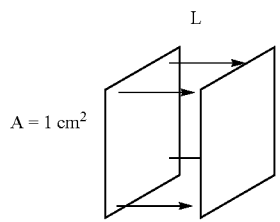

electrical field lines and the direction of electrical current are illustrated by the arrows. For parallel plate electrodes, the average Field Strength between the plates is V/L=100 Volts/1 cm=100 V/cm. The current between the plates depends on the impedance of the tissue in-between them. If this impedance is, say, 100 ohms, then the current between the plates is I=V/R=100/100=1.0 Amp. This would result in a Current Density of I/A=1000 mAmps/1 cm$^2$. For different electrode configurations and different tissue impedances, the relationship between Field Strength and Current Density will differ; however, they will approximately vary in proportion with each other. In the configuration of an elongate electrode and a ring electrode, the measure of Current Density can more readily be used to determine effective electroporation. This threshold has been experimentally measured in rabbit muscle to be near 300 mAmps/cm$^2$. Tissues which experience current densities above the threshold will be electroporated, and tissues below the threshold will not. By determining the boundary within a three-dimensional region of tissue that represents this threshold, the volume and shape within this boundary can be predicted to electroporate.

As shown in FIGS. 9A to F, the volume of tissue exposed to an electroporative pulse of energy can be essentially dialed-in without spreading of the electroporative energy beyond a measurable distance/volume of tissue. In FIG. 9A the prototype invention device was tested in New Zealand white rabbit leg quadriceps muscle pulsed at a 289 mAmps actual measurement correlating to a 64 V pulse, in FIG. 9C a larger tissue volume was electroporated using a 384 mAmps actual measurement correlating to an 81V pulse. In FIG. 9D a still larger tissue volume was electroporated using 579 mAmps correlating to a 103 V pulse, and in FIG. 9E a still larger tissue volume was electroporated at 758 mAmps measured correlating to 138 V. In FIGS. 9B and F both GFP fluorescence alone and GFP and visible light photos are disclosed showing the elecporative spread behavior of the treatment zone into the muscle tissue. In each of these experiments (FIGS. 9A, B, C, E and F) 280 ul (microliters) volume of GFP encoding plasmid DNA solution was injected into the rabbit muscle followed immediately by the requisite pulse. In FIG. 9D only 70 ul GFP DNA was used to show that electroporation will encompass all of the tissue volume containing GFP DNA (i.e., saturation of injectate not reached). Thus, in the FIG. 9D, actual electroporated volume measured is smaller (See Table II) than in FIGS. 9B and E even though in FIG. 9B the volume injected was about ⅔ more and electrical energy was less while in FIG. 9E the volume injected was about ⅔ more and electrical energy was more. The ring electrode conductive surface area for this experiment was approximately 25 cm$^2$ and the elongate electrode conductive surface area was approximately 0.22 cm$^2$.

The ring electrode surface area is correlated with the current density as shown in Table I below. Table I shows figures for a system equipped with an ovoid ring electrode having a surface area of 25 cm$^2$ and various applied field strengths.

TABLE I

| Elongate electrode (EE) surface area (cm$^2$) | Ring electrode (RE) surface area (cm$^2$) | Surface area ratio | Charge applied (Volts) | Electrode Current (mA) | Current density at EE (mA/cm$^2$) | Current density at RE (mA/cm$^2$) | Calculated EE Field strength (V/cm) at 11.4 ratio | Calculated RE Field strength (V/cm) at 11.4 ratio |
|---|---|---|---|---|---|---|---|---|
| 0.22 | 25 | >100 | 25 | 86 | 391 | 3.4 | 34 | 0.29 |
| 0.22 | 25 | >100 | 50 | 171 | 777 | 6.8 | 68 | 0.60 |

TABLE I-continued

| Elongate electrode (EE) surface area (cm²) | Ring electrode (RE) surface area (cm²) | Surface area ratio | Charge applied (Volts) | Electrode Current (mA) | Current density at EE (mA/cm²) | Current density at RE (mA/cm²) | Calculated EE Field strength (V/cm) at 11.4 ratio | Calculated RE Field strength (V/cm) at 11.4 ratio |
|---|---|---|---|---|---|---|---|---|
| 0.22 | 25 | >100 | 100 | 342 | 1554 | 13.7 | 136 | 1.20 |
| 0.22 | 25 | >100 | 150 | 514 | 2336 | 20.6 | 205 | 1.81 |
| 0.22 | 25 | >100 | 200 | 689 | 3132 | 27.6 | 275 | 2.42 |
| 0.44 | (Elgen) | na | 50 | 500 | 1136 | na | 100 | na |

Note:
Electrode Current is based on nominal tissue impedance per formula I = V/R of 292 Ω (calculated as an average of impedance measurements obtained for tissue between 231 Ω-380 Ω)

Table I shows calculations of current density at the ring (RE) and elongate (EE) electrodes. In these calculations, for the elongate electrode, the average of surface areas of hypodermic needles between a 22 gauge needle (0.7 mm OD Â 0.4 mm ID) and a 23 gauge needle (0.64mm. OD Â 0.1 mm ID) were used. Specifically, the various gauge needles have the following dimensions:
22 ga, 0.028"OD×25.4=0.71 mm
23 ga, 0.025"OD×25.4=0.64 mm
where Area=CL=πDL=3.14159×0.07 cm×1 cm=0.22 cm² (22 gauge needle, of the total length of the needle, the distal 1 cm was used in the calculations since it is that portion of the electrode that was non-insulated). The area of a 23 gauge needle is, for example, 0.20 cm².

Other gauge needles can be used such as, for example 24 ga, 0.022"OD×25.4=0.56 mm, 25 ga, 0.020"OD×25.4=0.51 mm, and 26 ga, 0.018"OD×25.4=0.46 mm. For each, the same type of ratios for current density can be generated, yet are not shown here.

Table I also shows current densities for an electroporation device (the Elgen electroporation device, Inovio Biomedical Corp., San Diego, as disclosed in U.S. patent application Ser. No. 10/612,304, filed Jul. 3, 2003, and herein incorporated by reference in its entirety) that uses two 2 cm length needle electrodes of 22 gauge having a surface area, of 0.44 cm², (all 2 cm non-insulated), thereby having a higher surface area than in the elongate electrode of the current invention. With respect to the Elgen device calculation, it is clear that the nominal field strength between two non-insulated parallel elongate electrodes at a distance of 0.5 cm remains at a high value (about 100 V/cm) capable of generating substantial nerve stimulation while the field strength at the ring electrode of the instant invention is on the order of 1/50th that value (between 0.29 and 2.42 V/cm).

The field strength applied (V/cm) can be interpreted as Volts between needle and ring electrodes at a closest distance (arbitrarily calculated at 1 cm) between them. For example, the distance between electrodes of the invention device can range between at least 1 and 4 cm, with 4 cm measured between the needle tip and the farthest outer edge on the ring electrode (here calculated for a 25 cm² ring electrode disclosed above). The exact "field strength" in V/cm between the elongate and ring electrodes cannot easily be calculated because the field strength is not constant between the electrodes but is diminishing from the elongate electrode towards the ring electrode surface which has a broad lateral profile. However, such calculation can be made for a system that employs parallel electrodes, such as in the Elgen device. In such a device current density (mAmp/cm²) and field strength can be determined because the electrodes represent well defined parallel sources of electric current, and because of the uniform nature of the field (simulating two parallel electrode plates). This ratio or relationship can be used to estimate an equivalent field strength for the ring electrode arrangement, at the strongest point next to the needle. This ratio is calculated for example as follows. A 50 V discharge across the Elgen device electrodes that are 0.5 cm apart results in a field strength of 100 V/cm. Using an impedance value for tissue of 100Ω between the two electrodes of the Elgen device results via the formula I=V/R=50/100=500 mA. Use of two 22 gauge needles of 2 cm length, and surface area of approximately 0.44 cm² results in a current density of I/A=500 mA/0.44=1136 mA/cm². Therefore the ratio between current density (1136 mA/cm²) and field strength (100 V/cm) is 11.4. This value is reflected in Table I.

The data in Table I shows therefore that with a ring electrode system of the present invention, the current density and field strength in V/cm can be reduced to a marginal value in areas of the body tissue, namely the skin tissues containing sensory nerve cells. At an applied voltage of 50 Volts, the V/cm experienced at the ring electrode is only 0.61 while an applied voltage of 100 V results in a V/cm at the ring electrode of only 1.2 V/cm. Even where the applied voltage is as high as 200, the V/cm at the ring electrode is only 2.4 volts. In contrast, applying only 50 V across the prior art Elgen device experiences a V/cm of 100 at both electrodes. Merely reducing the area of the electrically conductive portion of the elongate needles in an Elgen or other similar electrode arrangement, such as disclosed in any of U.S. Pat. Nos. 6,041,252, 6,278,895, and 7,245,963, such as by adding insulation to a portion of the electrodes will not lower the V/cm but in fact may well increase it. Thus, the use of insulation on the central electrode of the present invention is substantially different than as applied in prior tissue penetrating electrodes.

Figure 10A:
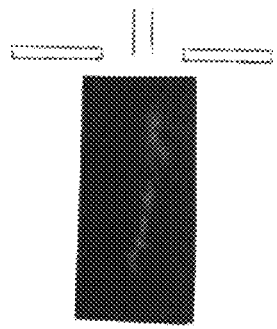
FIGS. 10A and B are color photographs showing GFP (FIG. 10A) and combined GFP and visible light (FIG. 10B) where tissue was subjected to a 189 mAmp/58 volt pulse using a ring electrode having a 2.5 cc surface area. As depicted the tissue volume is confined to tissue closely surrounding the elongate needle.
Figure 10B:
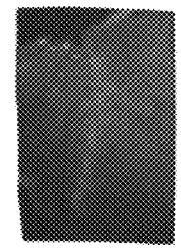

Additional examples of the instant invention wherein smaller ring electrode dimensions are used, such as where the surface area of the ring electrode is 2.5 cm, are shown to provide for the same control over the tissue volume intended for electroporation. With ring electrode embodiments wherein the ring has a relatively small diameter, current is directed less laterally through the tissue and more along the vicinity of the elongate electrode, similar to a non-ring single needle system, such as disclosed in pending U.S. patent application Ser. No. 11/804,703 herein incorporated by reference in its entirety. As disclosed in FIGS. 10A and B, an experiment in NZ White rabbit quadriceps muscle using a 200 mA setting (measured 189 mA and 58V) results in a narrow tissue volume being electroporated. Here the average current density at the elongate electrode was calculated at 189 mA/0.22 cm²=859 mA/cm² and the average current density at the ring electrode was calculated at 189 mA/25 cm²=7.6 mA/cm². Thus, whether the ring electrode is small or of larger dimension, the tissue volume undergoing electroporation can be experimentally predetermined, such as by measuring GFP expression in the tissue, and correlating the tissue volume electroporated to the injection volume/concentration of therapeutic substance.

Figure 7:
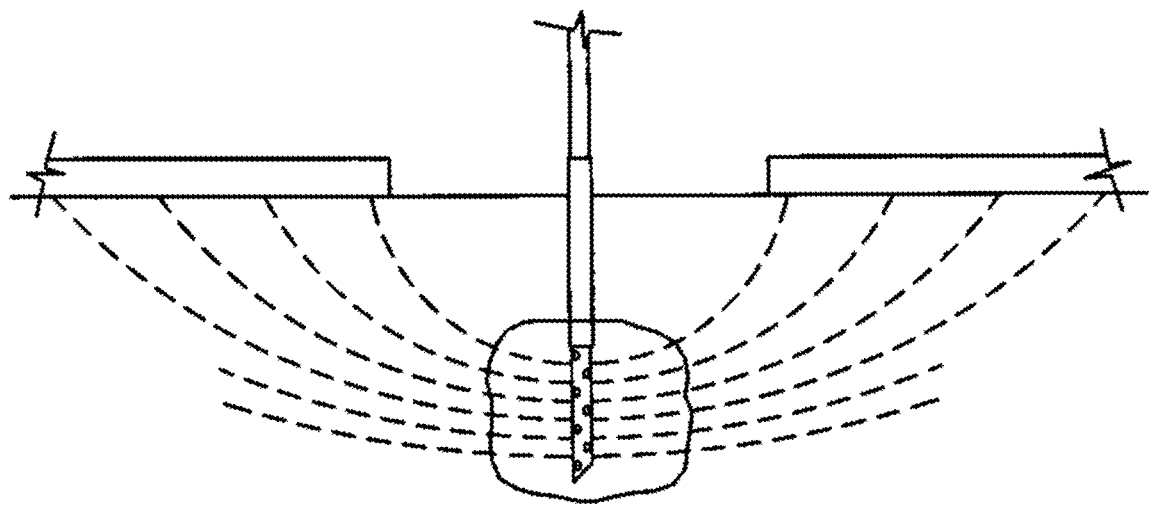
FIG. 7 is a schematic drawing of a likely shape of an electroporated bolus of delivered substance using the ring electrode system of the current invention.

Additional embodiments of the invention device include the capability of measuring the volume of tissue undergoing electroporation. This aspect provides a substantial advantage over prior electroporation systems in that it is now possible to predetermine the volume of tissue that will be exposed to an electroporative pulse of electric energy. Thus, the amount of substance delivered can be dosed to a predetermined tissue volume undergoing electroporation. As discussed herein, the ring electrode system provides for a variable current between the elongate and ring electrodes. This arrangement allows electroporation energy to propagate into the tissue away from the elongate electrode to a predetermined average distance and consequently measurable tissue volume (the length of the electrically conductive portion of the elongate electrode is known, the distance away from the electrode that electroporation has occurred as determinable by calculation and by prior empirical experimentation.) Both should correlate as shown herein. Since the lines of force from any electric pulse is directed generally outward from a central or core position and upward from the electrically conducting portion of the elongate electrode to the laterally positioned ring electrode, the actual electroporated volume of tissue will be generally cylindrical or even conical, cup or bowl shaped as depicted in FIG. 7. Further, the distance into the tissue the electroporative energy is propagated, is dependent upon the strength of the electric pulse and the natural resistance of the biological tissue. In a preferred embodiment, any level of electric energy pulse can be used having a value of between 1 and 200 V or alternatively, calculated for constant current, an amperage at the elongate electrode of between 0.01 and 1.0 amps.

Calculating the distance into tissue that an electrical field strength will be sufficient to porate cells, and consequently the tissue volume subjected to such field strength, can be accomplished empirically by measuring the amount of tissue subject to GFP expression. As shown in Table II, the volume of tissue affected does not correlate to the classic formula for calculating a cylinder or a cone volume. Rather, the volume affected is dependent upon the resistance of the biologic tissue and other physical parameters. Moreover, the volume undergoing electroporation is highly sensitive to the volume of GFP encoding plasmid injected into the tissue. As shown also in Table II, where one fourth the volume (70 ul vs 280 ul) is injected, the tissue volume undergoing electroporation is clearly greater than the region infused with a sufficient concentration of GFP plasmid. This can be calculated given that the greater current used (579 mA vs 384 mA) causes only about half the tissue volume expressing GFP, whereas, if an amount of GFP enough to flood the tissue were used (i.e., 280 ul), the tissue volume undergoing GFP expression would be between 1.4 and 1.9 cm$^3$. Thus, empirical calculations for volume of electroporated tissue must be conducted using a volume of GFP plasmid, or other like indicator, sufficient to completely flood the area of tissue being tested.

TABLE II

| GFP Injected bolus volume of equvalent concentration | Electric Current (mA) | Electric voltage (Volts) | Elongate electrode Length (cm) | Electroportion Maximum Radius empirically determined (cm) | Tissue volume actual (cm$^3$) % | Tissue volume cylinder# | Tissue volume cone $ |
|---|---|---|---|---|---|---|---|
| 280 ul | 189 | 58 | 2.0 | 0.1 (small ring)* | 0.1 | 0.1 | 0.03 |
| 280 ul | 289 | 64 | 2.0 | 0.4 (big ring)** | 0.4 | 1.0 | 0.3 |
| 280 ul | 384 | 81 | 2.0 | 0.5 (big ring)** | 1.4 | 1.6 | 0.5 |
| 70 ul | 579 | 103 | 2.0 | 0.5 (big ring)** | 0.9 | 1.6 | 0.5 |
| 280 ul | 758 | 138 | 2.0 | 1.0 (big ring)** | 1.9 | 6.3 | 2.1 |

Figures rounded to nearest $1/10$.
*small ring = 2.5 cm$^2$,
**big ring = 25.0 cm$^2$,
Theoretical based on classical formula V = bh = (pi × r$^2$)h;
$ Theoretical volume based on formula for cone volume V = $\frac{1}{3}$pixr$^2$h;
%-actual volume calculated using all slices of tissue having GFP staining.

With the ability to determine the likely volume of tissue undergoing electroporation, one can now align the volume/concentration of substance to be delivered with the volume of cells in the tissue that are available to take up said substance directly by the temporarily porated cells. This advantage allows for proper dosing and avoidance of over- or under-dosing and prevention of wasting of therapeutic materials. In other words, the current invention provides for the ability to deliver a calculated "effective dose" of, for example, an expressible nucleic acid based on knowledge of the volume of cells exposed to an electroporative pulse of any given current and nominal field strength, and knowing the volume of delivered material that is capable of being completely taken up by said cell volume.

The instant invention apparatus further comprises a mechanism for providing a charge of electric energy sufficient to cause electroporation in the tissue. In a particularly preferred embodiment, said mechanism comprises a capacitor situated in said apparatus having a capacitance of between 1000 and 2,200 uF (micro Farads). The capacitor can be placed in the device housing, such as for example in the portion comprising a hand manipulateable housing, and in electrical communication with the electrodes and the source of electric energy. In another preferred embodiment, the source of electric energy can be an external source such as stationary alternating current (wall socket), or a battery bank. Further, the capacitor can be energized in advance to a predetermined capacitance as desired for the specific treatment parameter to be used in any particular treatment regimen by charging it with a charging unit that is itself energizeable via the external source of energy. In a particularly preferred embodiment the capacitor is charged up to 200 Volts.

Circuitry Components

An electrical control circuit (not shown) is connected to both the elongate electrode needle 120 and the ring-shaped electrode 200 to produce desired electrical pulses sent from the capacitor, causing electroporation and electroporation-augmented delivery of the injected substance to cells in the target tissue.

The electronic circuit can comprise a battery, typically between 1.5 and 9 Volts, a capacitor that can store sufficient energy and voltage such that it can supply the desired electroporation output voltage for the desired output duration, and a control circuit that charges the capacitor to the correct voltage, and controls the output pulse voltage and duration.

Figure 6:
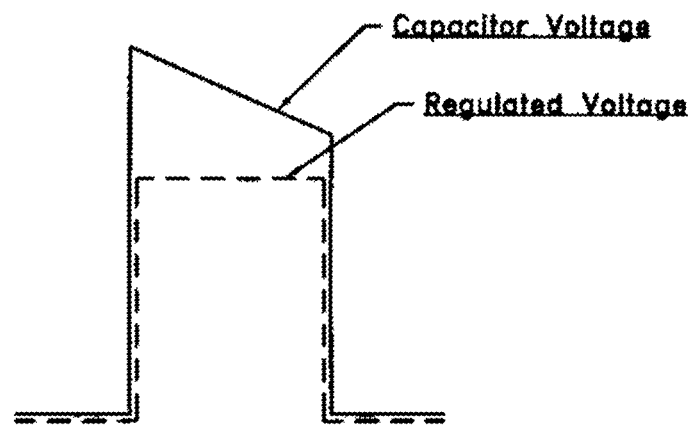
FIG. 6 is a graph depicting a regulated voltage potential generated from charging a capacitor to a higher voltage potential than actually employed during the pulse for the purposes of obtaining a relatively flat or constant voltage discharge.

In an exemplary embodiment, the circuitry arrangement provides for the electronic potential charging of a capacitor to a voltage that, when discharged for a set time period provides electronic energy pulses sufficient to electroporate cells in situ. The discharge of the capacitor can be regulated so as to provide for either bipolar discharge or monopolar discharge. For example, the discharge in a monopolar arrangement can be regulated to provide for maintenance of a set voltage pulse over the pulse time period. Specifically, in one embodiment wherein the device is set to generate 100 Volts for 100 milliseconds, for example, the pulse will have a wave form as depicted in FIG. 6. In such arrangement, the device is equipped with a capacitor capable of supplying, for example, 1 Amp for 100 milliseconds, and, at the end of this pulse, must remain above 100 Volts so that a voltage regulator using the capacitor's voltage to make the 100 Volt output does not drop out of regulation. By way of example, in one embodiment the invention device can comprises a 1000 microFarad capacitor. As is well understandable by one of skill in the electric arts, equation V×C=Q describes the energy needed to obtain a 100 Volt output where V is Volts, C is micro Farads, and Q is Coulombs. Specifically, in order to obtain a discharge with a regulated constant 100 V potential over the 100 millisecond pulse, the voltage charge to the capacitor must be 200 Volts, i.e., V=200, C=2200, Q=0.44 based on the formula Q=CV. In a variation of this embodiment, there could be a succession of two or more pulses, at the end of which the capacitor's voltage is still above the 100 Volts so that the output does not drop out of regulation for any of the pulses within the succession.

Virtually any capacitor value can be used for a circuit employed in the current invention device. For example a 100 uF (microFarad) capacitor used to discharge 0.1 coulomb of electric charge requires the capacitor to be charged to 1000 Volts above the regulated target voltage to the patient. Alternatively, the same discharge can be accomplished with a 10,000 uF capacitor charged to only 10 Volts above the regulated target voltage. In the case of the current invention, in one embodiment a capacitor having a capacitance of about between 2000 to 4000 uF can be used which will in such case provide for a 100 millisecond pulse of 100 Volts. The voltage required to supply the aforementioned pulse is approximately 150 Volts depending on the tissue impedance between electrodes.

In one embodiment of the invention device, the circuit comprises 1) a microprocessor to control the charging and discharging process, and to manage a control and safety circuit; 2) a charging circuit that is controlled by the microprocessor and that brings the capacitor to the calculated correct voltage for the desired electroporation pulse time period wherein when the capacitor reaches the desired voltage potential the microprocessor turns off the charging circuit; 3) the charge capacitor; 4) a linear regulator controlled by the microprocessor that can be turned on and off quickly so that it can supply pulses of voltage and duration programmed into the microprocessor; 5) safety and monitoring circuits that protect the circuit from abuse and also check and guarantee that the voltage only appears on the output when it is requested, for safety.

In further related embodiments, the charging circuit can comprise a current limited fly-back regulator. In such a circuit, the regulation voltage is set to a value higher than required for any voltage level used to electroporate tissue. The current limit allows optimization of the lifetime of a battery. If the charge is taken from a battery too quickly the battery life is significantly shortened. To maximize battery life, the current limit on the regulator is set for short charging times. In the case of a 9 Volt battery, for example, the optimum current is approximately 200 mA, and for a 100 Volt, 120 millisecond electroporation output. In this case the charge times are around 15 seconds.

In further embodiments, the capacitor is charged to an optimum voltage required by the linear regulator such as a charge to volt ratio ($V_{out}$) as in the following formula, (1+4.5 t)+10 Volts, where $V_{out}$ is the electroporation output voltage and t is the total electroporation pulse duration (i.e., the sum of the times for all the electroporation output pulses). By charging the capacitor to the voltage described by this equation, the circuit has a minimal amount of energy lost that is not delivered to the electroporation process.

In another embodiment, a wideband linear regulator can be used wherein the voltage reference used to determine the output voltage is supplied by a pulse width modulation circuit within a microprocessor. When the circuit is off, the microprocessor derived pulse width modulation duty cycle is zero. For the electroporation pulse duration, the pulse width modulation output from the microprocessor is set to a value corresponding to the desired regulated value, that is, the average value times the gain of the regulator which equals the pulse output value. At the end of the desired electroporation pulse, the pulse width modulation output is again set to zero.

In further embodiments, the invention device circuitry comprises safety and monitor circuits. A safety switch in this circuit can turn off the output in the event of any detected failure. In this embodiment the microprocessor measures the output voltage before the pulse is to be applied to the electrodes. The processor then measures the output pulse voltage magnitude during the pulse. In a preferred embodiment the voltage measurement must be within 10% of the intended voltage output. The microprocessor further measures the current of the pulse and also measures the voltage at the end of the pulse to verify that the pulse terminated properly. With regard to each of the tested conditions noted above, if any such conditions are not within specified parameters, the device's ability to pulse is terminated and the user is advised of a system error. Types of failure can be: output short circuit, output voltage incorrect, output period too long, and the like.

In still further embodiments, the control microprocessor contains software programming capability, including parameters for the analog-to-digital inputs, and the control lines to charge and discharge the storage capacitor to manage the circuit as described. The device circuitry further includes EEPROM (Electrically Erasable Programmable Read Only Memory) to allow the user, by using a computer interface, to change the pulse timing and settings recorded in the software, thereby changing the output pulse durations and levels. In further embodiments, output values for pulsing can be saved even if power to the board is removed. The values are check summed to not allow erroneous values to control the outputs.

The waveform of the electrical signal provided by the electrical power source can be an exponentially decaying pulse, a square pulse, a unipolar pulse or pulse train, a bipolar oscillating pulse, or a combination of any of these pulse forms. The nominal electric field strength can be from about 10 V/cm to about 200V/cm corresponding to current of approximately 0.05 Amps and 1.0 Amps, respectively. Many different specific pulse energies can be employed such as for example, 10V/cm, 15V/cm, 20V/cm, 30, 40, 50, 60, 70, 80, 90, 100, 110, 120, 130, 140, 150, 160, 170, 180, 190, and 200V/cm. Each of such pulse voltages and field strengths have a corresponding current density at each of the elongate and ring electrodes and corresponding volumes of tissue that will be subject to pulses of electricity sufficient to electroporate cells.

Pulse length can be about 10 microseconds to about 100 milliseconds. In particular, specific ranges and times can be used such as, for example, 10 milliseconds, 20 ms, 30 ms, 40 ms, 50 ms, 60 ms, 70 ms, 80 ms, and 90 ms. There can also be any desired number of pulses, typically one to 100 pulses, more typically 2 to 6 pulses, even more usually 2 to 4 pulses. The time interval between pulses can be any desired time, such as one second or less, more typically 10 milliseconds or less, even more usually 5 milliseconds or less. The waveform, electric field strength and pulse duration may also depend upon the type of cells and the type of molecules that are to enter the cells via electroporation. Each pulse wave form has particular advantages; square wave form pulses provide increased efficiencies in transporting compounds into mammalian cells in comparison to exponential decay wave form pulses. Preferably, the waveform used is an exponential or a square wave monopolar pulse.

In addition to the ring electrode assembly and attendant circuitry components as disclosed above, the invention apparatus can have a variety of further functionalities. For example, the apparatus can have a data display for indicating apparatus function and status settings, the various pulse parameter settings including, for example, voltage, capacitance, pulse duration, time delay between pulses, pulse wave type, number of pulse(s) applied, and parameters of the applied pulse(s) (e.g., voltage, capacitance, pulse duration, pulse wave type, number of pulses), or combinations thereof. Such display can be visual, audible, or combinations thereof. For example, a single audible "beep" can indicate that the "apparatus is ready," two audible "beeps" can indicate that a pulse has been correctly applied and three audible "beeps" can indicate a malfunction or that the pulse was not or was improperly applied. Visual displays include analog or digital alpha-numeric displays (e.g., LCD, LED and the like), as in watches, and further can include illuminating means for low light visualization, for example, by white light, electroluminescent backlighting for LCD or electroluminescent lamps (i.e., INDIGLO.™.), or by various fluorescent or radioactive illuminating compositions, and the like.

Additional "user friendly" functions include controlling means such as software for controlling electric pulses as well as means for adjusting parameters (e.g., by pushbutton, knob, lever switch, dial and the like) including, for example, pulse duration, voltage, capacitance, field strength, number, wave type, and the like. Means for adjusting, setting, storing or retrieving one or more pulse parameters also are included herein. Such means include traditional mechanical electronic controls (e.g., a selector switch controlling each parameter in which the switch has a plurality of settings; exemplary pulse length settings, 5 msec, 10 msec, 25 msec, 35 msec, 50 msec, for example) as well as a chip control (e.g., silicon wafer types commonly used in the computer industry) which is controlled, for example, by a pushbutton interface, as in watches for example. A chip, optionally removable from the apparatus, for user and/or manufacturer programmable settings for control of the various pulse parameters set forth herein also is contemplated. Storage capacity of such a chip is sufficient to provide virtually unlimited fine control of the various parameters, as well as storing different pulse parameter settings for different compositions, users and the like. As each of the various electronic functionalities of the invention apparatus described herein can be controlled or managed by a computer chip, a chip affords the option of additionally incorporating software, if desired, said software optionally user programmable.

In addition to the above described user-friendly attributes, the invention apparatus provides for safety controls. Thus, in another embodiment, the invention further provides a means for preventing applying excess pulse voltage, duration, field strength and/or number of pulses. Any means which passively or actively interrupts or disrupts the electric circuit, including fuses, circuit breaker switches, and the like, or devices that actively monitor the various pulse parameters and interrupt or disrupt the electric circuit to prevent excess pulse voltage, duration, field strength, pulse number from being applied can be incorporated into the circuit path. Those skilled in the art of electrical devices will know how to incorporate such features as well as other protective elements that prevent applying excess pulse voltage, duration, field strength or number.

The present invention further provides for an advanced method of performing the injection of therapeutic from the device's central needle into the target tissues. Specifically, the invention device, being equipped with drivers and actuators for driving the injection needle into the tissue and for injecting the therapeutic from a reservoir through the needle, is designed to sense the tissue type the needle is entering, essentially determining interface points between tissue types. This expressly allows the user of the device to deliver with confidence the substance into specific tissues. Historically, vaccines have been delivered to subcutaneous muscles by hand injection in order to achieve adequate immune responses. However, if the vaccine becomes deposited in the fatty layer (adipose tissue) above the muscle, the resulting immunity can be compromised and lead to too low a titer to fight the infection the therapy for which the vaccine was intended. It is well understood that different length needles are necessary to reach muscle tissues in humans. Without proper medical training incorrect length needles can be improperly used. Even for many $1^{st}$ generation automated injection devices, proper delivery cannot be achieved simply due to not having any way to determine proper needle insertion for delivery to specific tissues such as muscle tissue.

In the present invention, the device is capable of sensing and determining when the injection needle enters the muscle tissue after which injection of the therapeutic substance is begun. In a preferred embodiment, sensing is done by measuring the electrical impedance of the tissue as the needle enters the tissue surface. As the needle is inserted into the tissue, the impedance of the tissue is measured at small increments using small, highly tolerable electrical pulses of a volt or less (even likely to be imperceptible). The impedance will change according the characteristics of each tissue type and depth of insertion. Generally the impedance of muscle tissue is lower that of dermal and adipose tissues. As a lower resistance zone is reached, the resistance drops accordingly. The nature of the resistance readings can be applied against a data base of tissue types from historical data and by such comparison establish the likely tissue type and interface of each specific injection, in the present case the interface between adipose and muscle tissue. In a preferred embodiment, the device can be designed to not begin delivery of the therapeutic from the reservoir until the needle has traveled into muscle a small distance. This allows a reasonable buffer zone of muscle at which point the injection may safely begin in the desired tissue type. In a preferred embodiment, injection of therapeutic is begun after entry of the sensed muscle tissue and continued while the needle is being further inserted so as to result in uniform injection over a fixed distance, preferably about 1 cm, resulting in a column of drug in surrounding tissue about the needle. This is an ideal condition for further electroporation as the maximum amount of drug is near the electrode and in the target tissue. Alternate methods of measuring tissue thickness can be used including high frequency signals administered through similar probes and ultrasonic sensors, to mention only two.

Figure 14A:
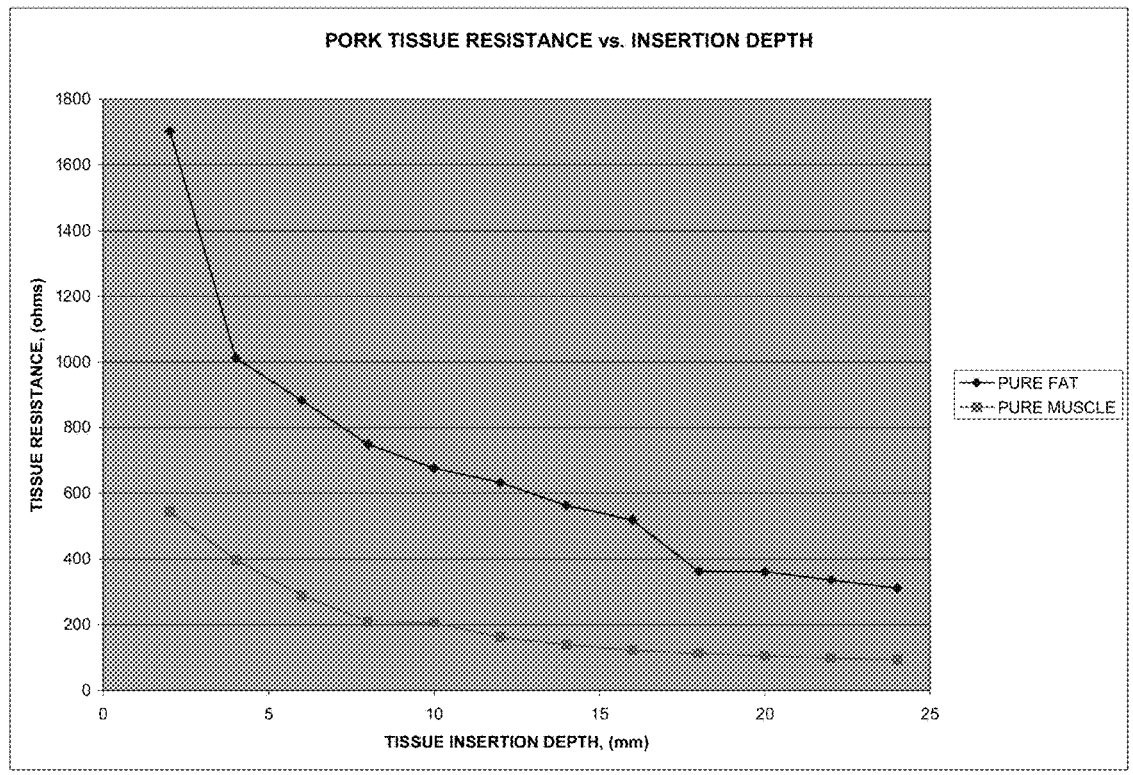
FIGS. 14A, B, and C are graphs depicting the sensing of divergent tissue type interfaces, specifically adipose or fat tissue and muscle tissue.
Figure 17A:
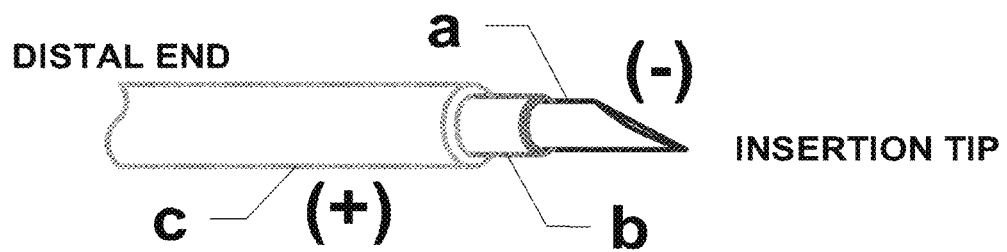
FIGS. 17A, B, C and D are diagrams showing construction examples for needles useful for sensing tissue resistance for determining tissue interfaces.
Figure 17B:
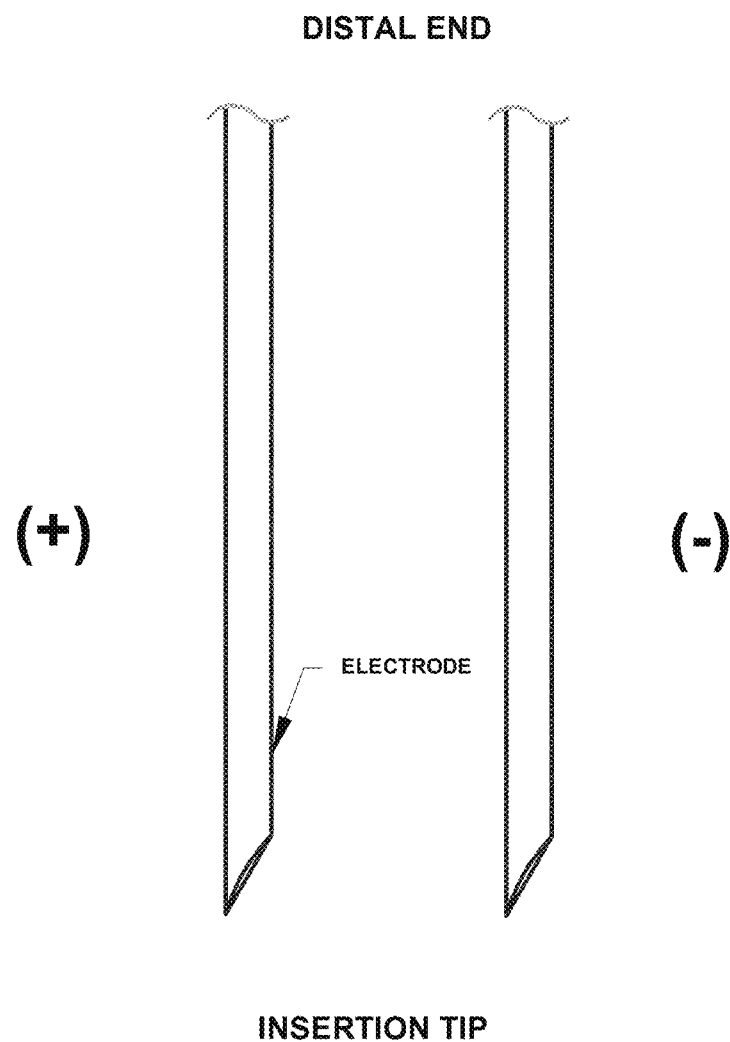
In FIG. 17B, a dual needle arrangement is depicted wherein the central needle of the current system is actually two closely spaced delivery tubes and each can act as individual electrodes.
Figure 17C:
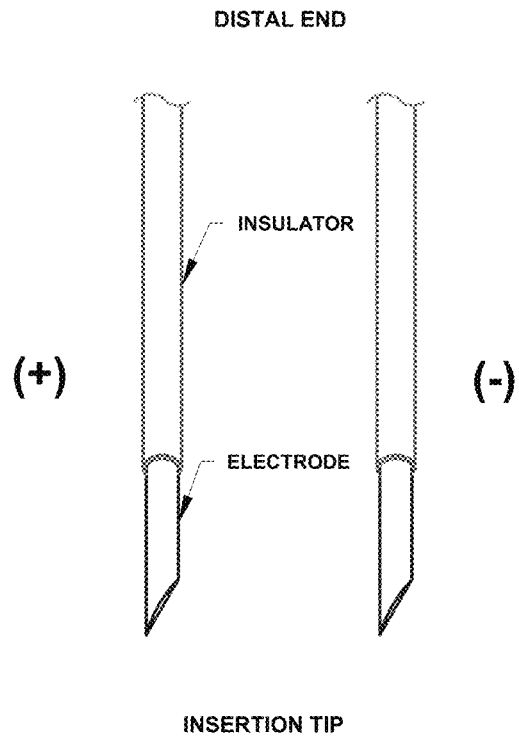
In FIGS. 17C and D, two additional design formats are depicted for a double central electrode system.
Figure 17D:
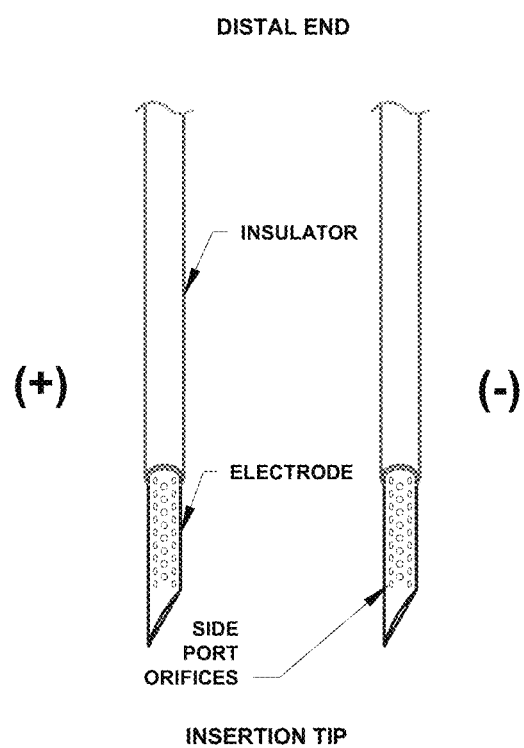

Tissue type sensing methodology of the current invention is described in FIGS. 14A, B and C and further below. Brief, low voltage (about 1 V or less) or low current pulses are sent through the insertion needle at small incremental movements (0.1 mm to as much as 2 mm insertion length increment) during the insertion of the needle. Sensing can be programmed for sensing to a total travel length of about 2 cm. In the current invention, the central needle can be constructed to possess two electric poles, i.e., a positive and a negative lead) placed near the end of the needle. Specifically, the needle itself can act as one pole while the second pole is attached at a nearby second location as depicted generally in FIG. 15A elements 400 and 401. FIG. 17A is a detailed representation wherein the needle is constructed with two electrical leads A and C separated by an insulation material B. Alternatively, tissue sensing can be performed in another format wherein the central needle is actually two closely spaced parallel injection needles (as depicted in FIGS. 17B, C and D). In such arrangement, the individual needles can act as separate electrodes for sensing tissue resistances. Further, in such configuration whereas during tissue sensing the electrodes are opposite polarity, during the electroporation step, the two needles can be pulsed both the same polarity and the opposite polarity will be the ring electrode. Further still, this methodology of sensing tissue interfaces is applicable to any system employing electroporation where the type of tissue sought for delivery of therapeutic substances is critical to their efficacy. Nucleic acids are of this type therapeutic. The DNA must be delivered into cells of the muscle compartment, as opposed to adipose tissue, to properly function. Thus, use of the tissue sensing methodology of the present invention is applicable to uses with electroporation devices that employ at least one tissue penetrating delivery tube. Where a single needle is employed, it must be designed with two electrode poles. Where more than one tissue piercing needle is used, separate needles can be used for tissue type sensing. In either case, the delivery/sensing electrodes can have insulation and fenestrated ports.

Figure 14B:
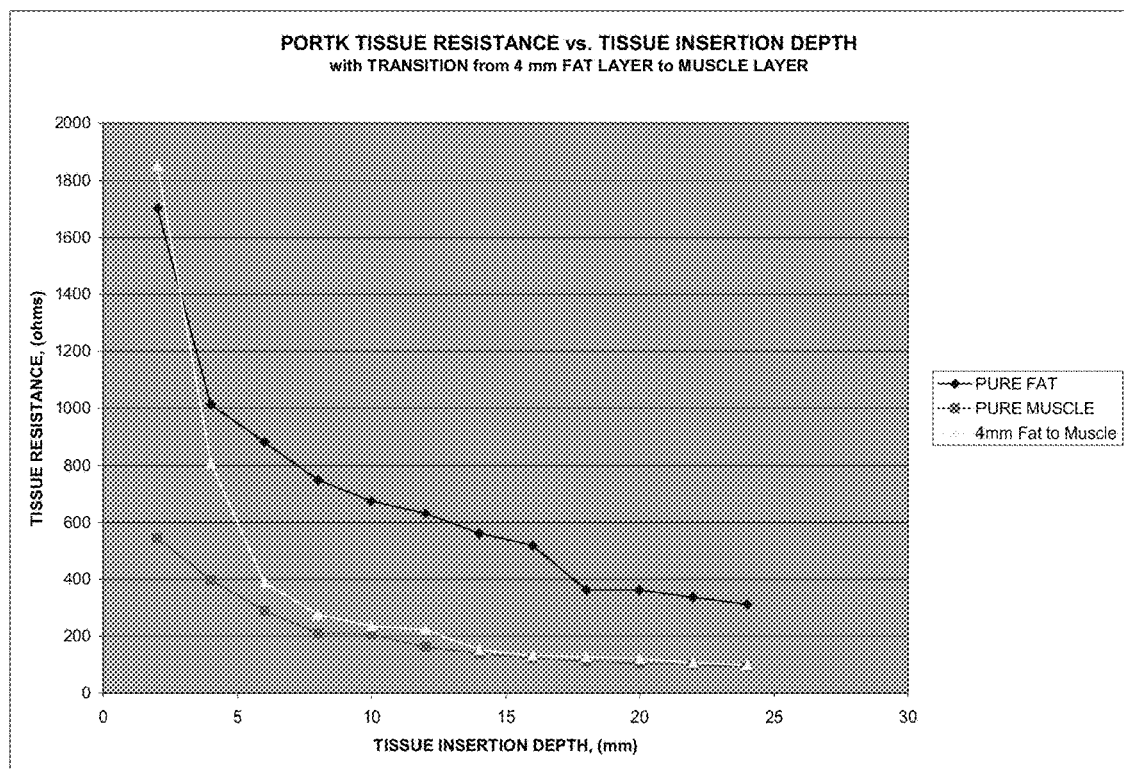
Figure 14C:
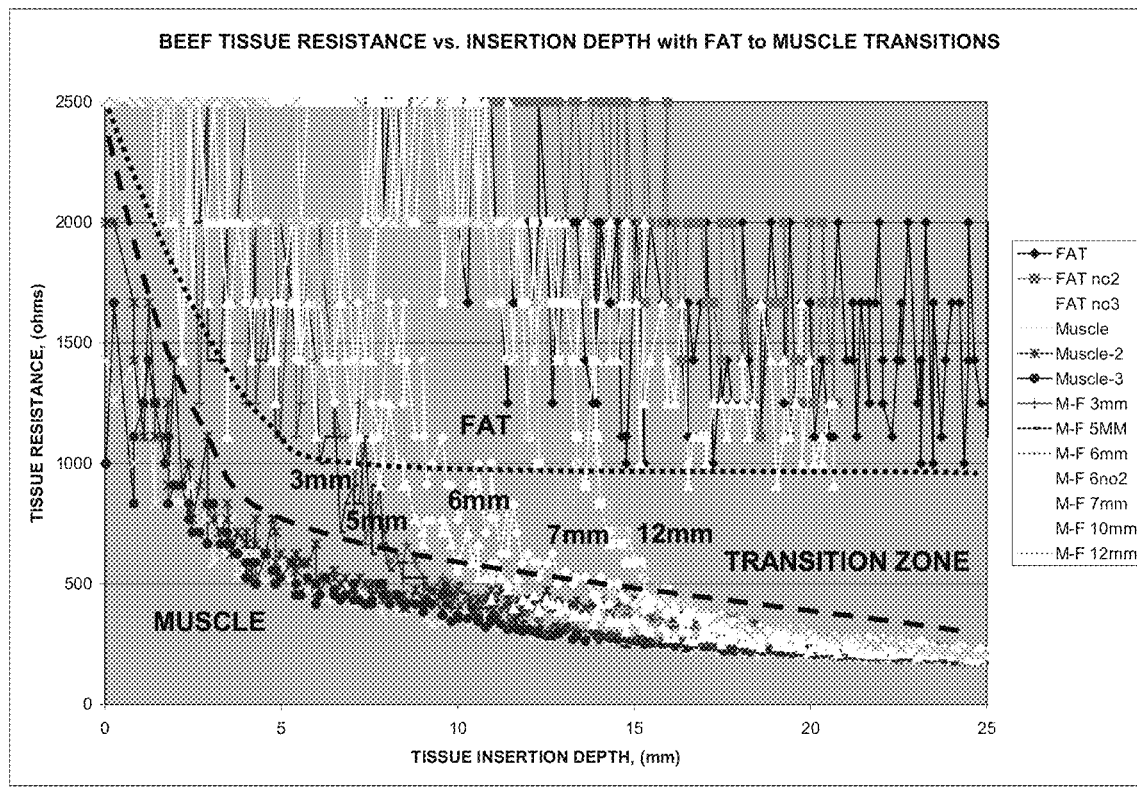

Electric pulses use to sense tissue resistance only need to be long enough to allow for an accurate sampling of the voltage and current from which the impedance can be calculated using Ohm's law (V=IR; V is volts, I is current in amps and R is resistance in ohms). A pulse length of 20 msec can satisfy these requirements for a typical needle insertion rate. If the probes are inserted into a uniform infinite substance the resistance will decrease asymptotically with depth to the characteristic resistance of the material, with a small influence of the needle diameter and conductivity. Tissue layers behave in this way as seen in FIG. 14A where needle probes were inserted into a pork fat layer that initially measures approximately 1700 ohms and decays to approximately 300 ohms. A second curve in FIG. 14A shows needles inserted into a pork muscle layer and shows lower impedance that decays to near 100 ohms. These measurements were obtained using a 21 gage, 2 inch needle and measured at 2 mm increments from the tissue surface to a depth of 24 mm. The test pulse was 100V at 20 msec for each increment. Graphing the sensing through a multi tissue type layer such that the needle is driven through a layer of fat followed by underlying muscle results in curves that initially match that of fat, but soon transition to the curve associated with muscle. FIG. 14B adds curves from insertions through fat layers of 4 mm thickness followed by muscle tissue using the same pulse and measurement parameters as above. Notice that as the lower impedance of the muscle is reached the measurements quickly transitions from the fat curve to the muscle curve. A similar experiment was performed on non-viable beef using an automated needle inserting device with measuring pulses generated at define increments. Pulses of 10V with durations of 50 msec were used to measure the generated current at approximately 0.2 mm increments along a continuous needle insertion. FIG. 14C shows similar curves or zones for the pure fat and muscle. Pure fat initially reads approximately 2500Ω and decays to approximately 1000Ω at 5 mm to 10 mm of insertion depth. Pure muscle initially reads between 1000 and 2000Ω, but quickly decays to 500Ω by 5 mm of insertion depth and to approximately 250Ω beyond 15 mm of insertion depth. This graph shows that it is possible to use historic data for fat thicknesses to determine the optimal position at which to determine that a tissue interface has been passed (particularly the adipose/muscle interface) and that injection can begin in the desired tissue.

The invention device can be programmed to begin injection of the therapeutic by using tissue type sensing information several ways. For example, injection can be commenced upon sensing indicating that there is a decrease of resistance to a reading equal to that of the muscle curve, resulting in delivery of substance a relatively large distance into the muscle tissue from the actual muscle/adipose interface. Alternatively, resistance values based on depth that would correlate to muscle or that correlate to a rapid drop in resistance inconsistent with asymptotically decays can be used as the signal at which to begin injection. Once the transition to muscle is determine by any of the above methods of adequate sensitivity, the injection process begins with one of the previously described sequences. The resistance measurements are no longer required nor performed if additional insertion is desired, just driving of the needle into the tissues further, if desired, while injecting the therapeutic.

Figure 15A:
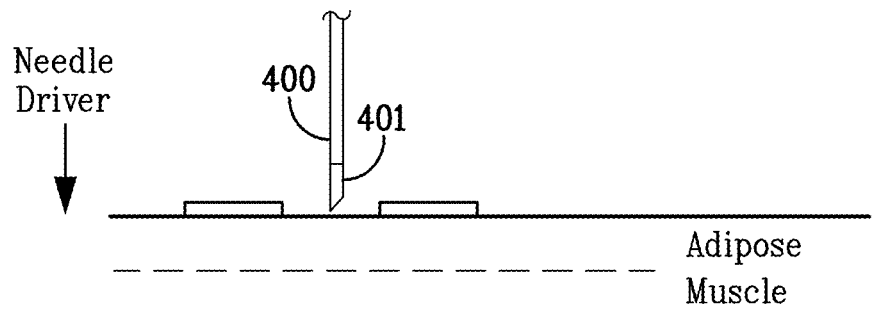
FIGS. 15A, B, C and D are pictorial diagrams showing the process of sensing tissue types followed by simultaneous driving of the needle into tissue while injecting the injection substance.
Figure 15B:
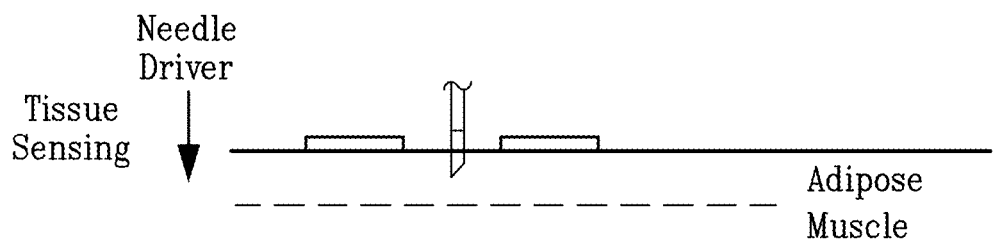
Figure 15C:
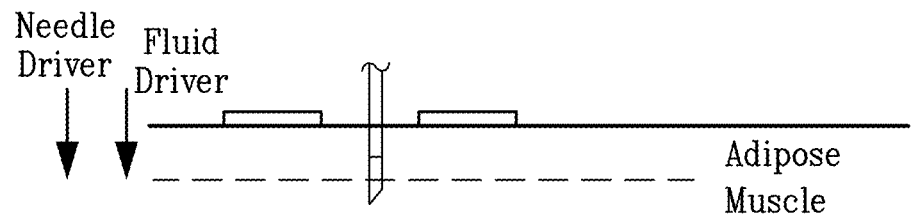
Figure 15D:
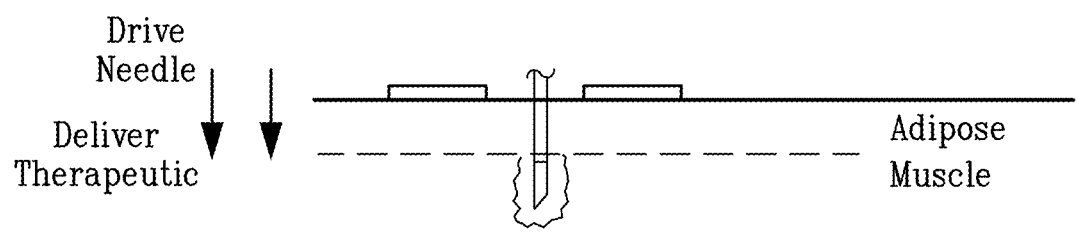
Figure 16:
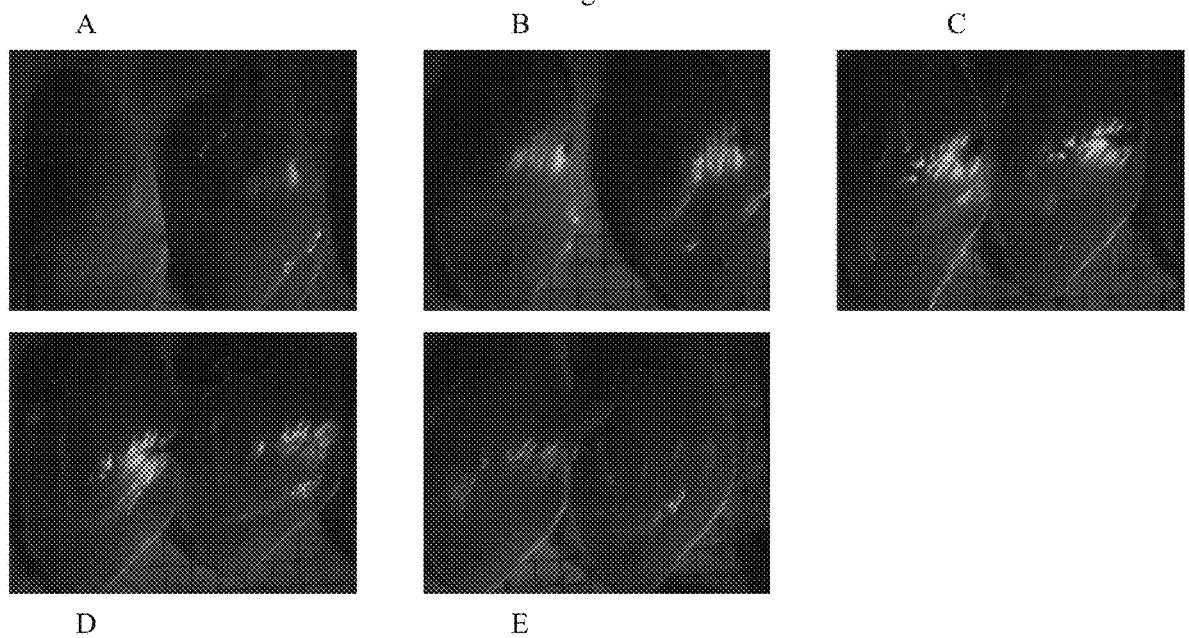
FIGS. 16A-E are GFP staining photographs showing the successful electroporation of animal muscle tissue using the ring electrode having a plurality of projections. Each successive photo is that of adjacent tissue slices.

Still further, since the apparatus of the invention includes such embodiments as tissue interface sensing, the device can include animated or inanimate/motor driven mechanical actuators for independently driving the elongate needle forward into the tissue to be treated without simultaneously driving the injection substance through the tubular needle. Particularly, the drivers can drive the needle into the tissue, while software is employed to sense electrical resistance in the tissue at the needle tip. A pictoral diagram of this methodology is provided in FIGS. 15A-D. In FIG. 15A, the apparatus is set for sensing tissue interfaces as the actuator for driving the needle directs the needle into the tissue. In FIG. 15B, when the needle passes the tissue interface, software directs the apparatus to continue driving the needle into the tissue a predetermined distance past the detected tissue interface. In 15C, when the sensors detect that the tissue interface has been passed, the apparatus, as one of ordinary skill in the art will appreciate, can be programmed to begin injecting the injection substance as the needle is driven further to a terminal position within the tissue (FIG. 15D) providing for a relatively evenly distributed injection substance. This aspect requires that the apparatus at this position has the ability to simultaneously drive the needle forward into the tissue this time simultaneously with the injection of the substance to be delivered into the tissues.

With respect to the ring electrode, as mentioned earlier in FIG. 13, the electrode can be designed specifically for use in animal husbandry. Specifically, since herd animals, such as cattle, sheep, goats, and horses, have a hair, fir, or wool covered body, the ring electrode designed for contacting skin surface will not be useful without having to shave the pelt from the animal prior to treating the animal. Since such a requirement is troublesome in large herd operations, shaving the pelt is not an option. Thus, the present invention provides an alternate design for the ring electrode. In a preferred embodiment, the ring electrode for animal use can be designed with a plurality of short nontissue piercing projections which easily can be pushed against the animal's fur/hair/wool covered hide and find their terminal portions contacting the skin through the pelt cover. In keeping with the various elements of the current invention, the ratio between the surface area of the conductive portion of the central tissue piercing needle and the total surface area of the tips of the projections should be maintained at between at least 1:5 and 1:10, respectively.

Figure 13A:
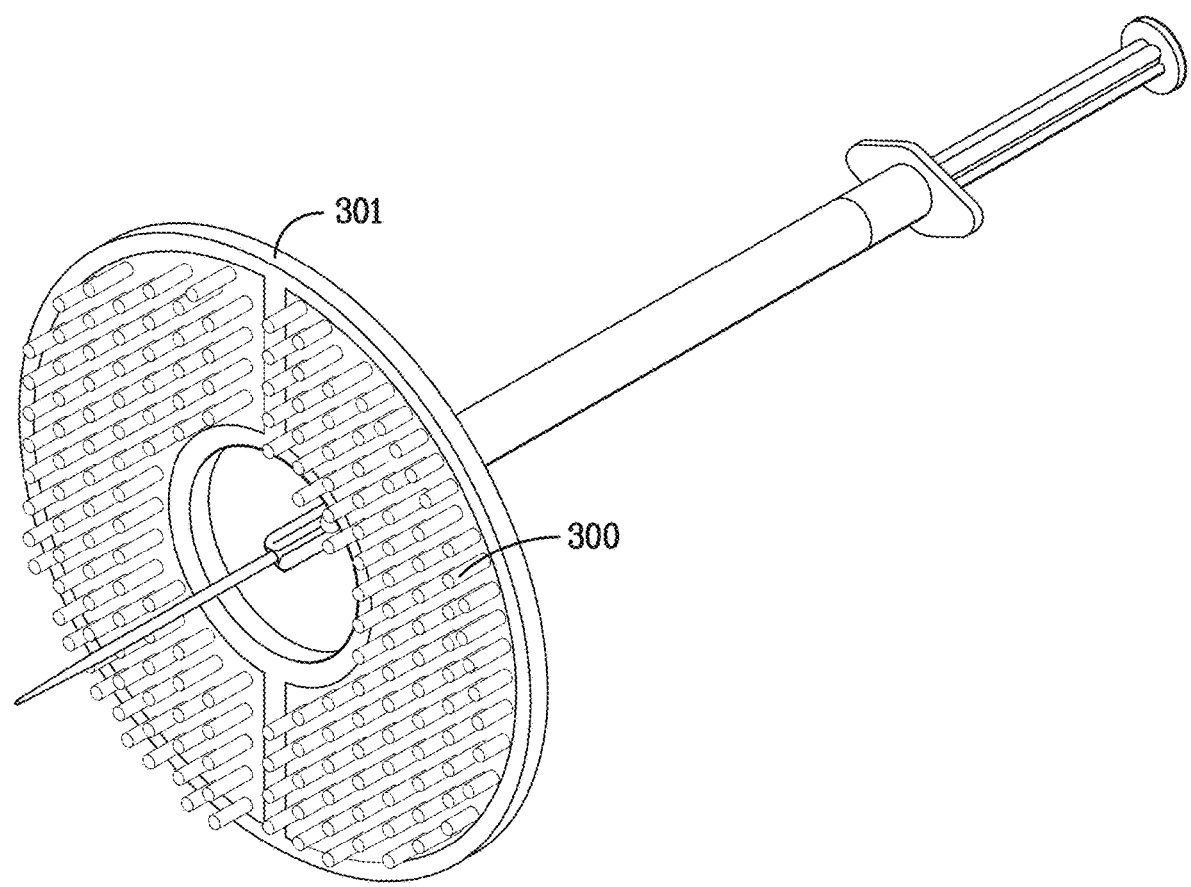
FIGS. 13A and B are perspective drawings of alternative ring embodiments designed for use in delivering electroporative pulses to hair, fur, or wool covered domestic herd animals. In this embodiment, the ring 301, whether round, ovoid, split or not, is equipped with a plurality of electrically conductive projections 300 that can penetrate a hair, fur, or wool coat to contact the animal's skin surface.
Figure 13B:
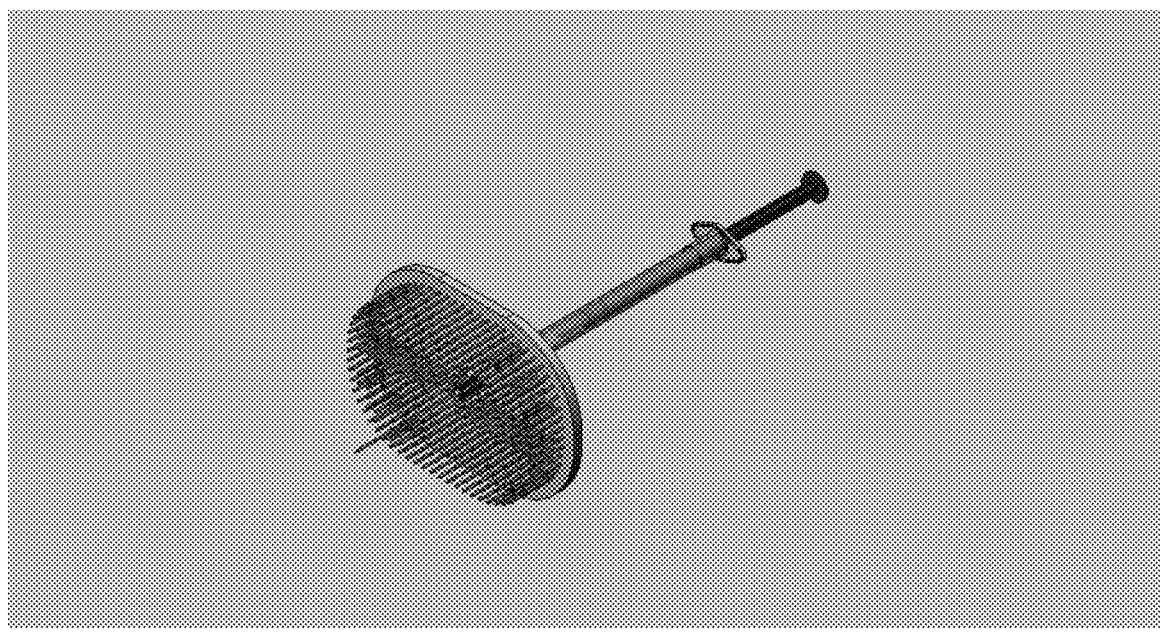

As shown in FIG. 13, the ring electrode comprising a multiplicity of projections is capable of electroporating pelt covered animals. As shown in FIGS. 16A to E, the electroporation is extensive. FIGS. 16A to E are adjacent slices of muscle tissue electroporated using the ring electrode having said projections and using 758 mAmps, 138 volts, and an electrode surface area ratio of the needle:projection area electrode arrangement wherein said ratio was at least 1:5. In this experiment 30 ug of gWiz-GFP in 300 ul saline was injected into rabbit quadriceps muscle followed by electroporation. The rabbits were sacrificed at day 5 and muscle samples were subject to sectioning at 1.25 mm thicknesses and analysis by fluorescence microscopy. These results are comparable to those shown in FIGS. 9E and F using the same pulse conditions.

Figure 18A:
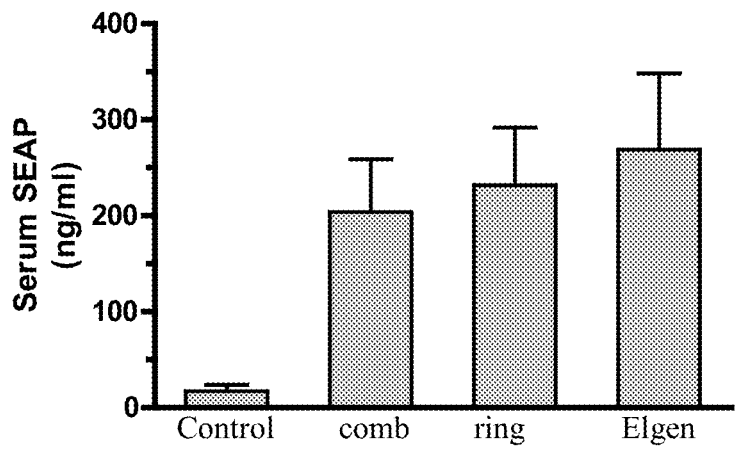
FIGS. 18A and B are graphs showing in FIG. 18A results of expression of plasmid gWiz-SEAP, a plasmid encoding secreted alkaline phosphatase, following electroporation in rabbit tissues using the methods and devices of the invention, namely use of a planar ring electrode and a ring electrode with projections (comb electrode). Also depicted are control negative and control positive using an elgen device.
Figure 18B:
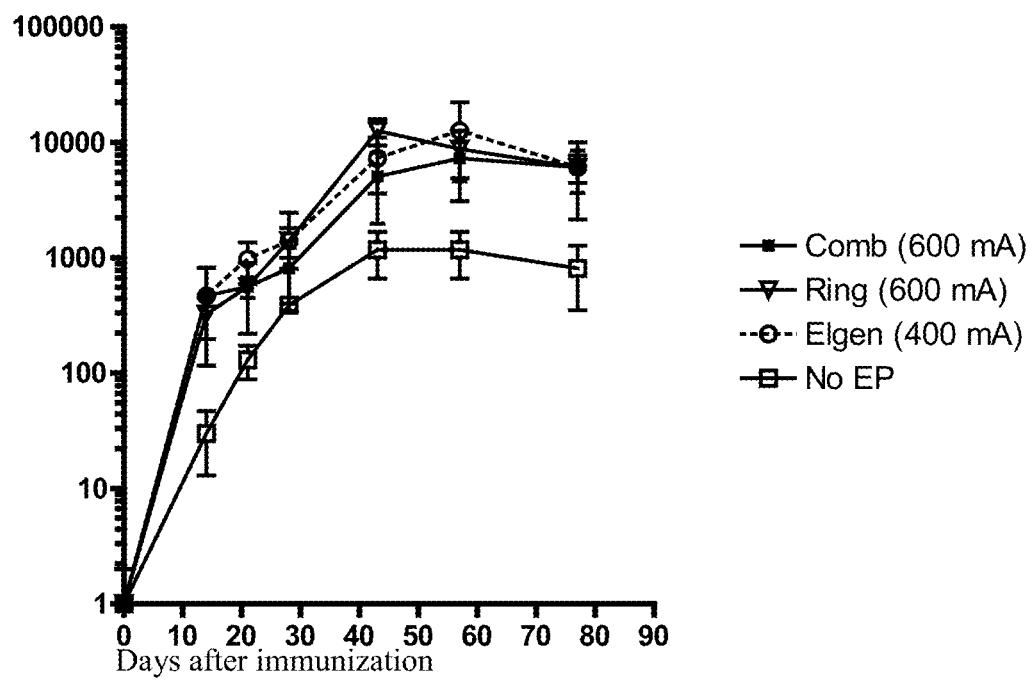
In FIG. 18B induction of anti-HBsAg antibodies in rabbits is shown for the same electrodes using same delivery conditions.

The electroporation carried out above was also performed on animals to test expression of SEAP and immune response to plasmi-enodded Hepatitis B antigen. As shown in FIG. 18A, an electroporation experiment was performed using the ring electrode, a comb ring electrode and a two needle electroporation device (Elgen, Genetronics, Inc. San Diego Calif.). as indicated, the electroporation and resultant SEAP expression is comparable for each of the ring, combed ring and Elgen. Plasmid gWiz-SEAP was injected at 200 ug in 300 ul saline. The control had Injection only with no electroporation. Pulsing parameters for each were as follows, Comb: 600 mA, 2 p×60 ms; Ring: 600 mA, 2 p×60 ms; Elgen: 400 mA, 2 p×60 ms. In FIG. 18B, anti-HBs IgG expression was tested by looking at endpoint titers. Plasmid gWiz-HBsAg was injected using 300 ug of plasmid in 300 ul saline with an initial immunization at day 0 followed by a boost at day 30. As indicated all of the test experiments show that the present invention, whether using a plain ring electrode or a combed electrode, works very well.

Methods

In accordance with the present invention, there are provided in vivo methods for introducing a therapeutic agent into subdermal and deeper body tissues, particularly striated and or smooth muscle cells, within these tissues. Methods of the invention comprise applying a pulsed electric field to said cell-bearing tissues substantially contemporaneously with the application of said delivery substance to said tissues, such that said delivery substance is introduced into said cells.

In a related embodiment the present invention provides a method for the introduction of nucleic acid into the cells of the dermis and muscle, preferably human, by delivering the nucleic acid to the targeted tissue and applying at least one electrical pulse to the targeted region. The electrical pulse is of sufficient voltage and duration to cause electroporation so that the nucleic acid can penetrate into the cells and the polypeptide encoded thereby to be expressed as a transgenic molecule. The biological expression of the nucleic acid component results in the transcription and translation of the delivered gene so that the targeted cells synthesize gene product de novo. Therapeutic applications include, for example, the augmentation of missing or under-expressed genes; the expression of genes that have a therapeutic value (e.g., inhibiting the action of harmful gene products by expressing a receptor to bind the product of an over-expressed gene); the expression of genes, the product of which elicits a desired immune response; and the like.

As will be understood by those of skill in the art, efficient expression of a nucleic acid encoding a therapeutic polypeptide generally requires that the nucleic acid sequence be operably associated with a regulatory sequence. Regulatory sequences contemplated for use in the practice of the present invention include promoters, enhancers, and the like. As those of skill in the art will also appreciate, even when a promoter sequence is operably associated with the therapeutic nucleic acid, expression may be further augmented by operably associating an enhancer element or the like.

It may be desirable to modulate the expression of a gene in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, for example, nucleic acid sequences that interfere with expression of the gene at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Nucleic acids contemplated for use in the practice of the present invention include naked DNA, naked RNA, naked plasmid DNA, either supercoiled or linear, RNAi, siRNA, microRNA, and shRNA and encapsulated DNA or RNA (e.g., in liposomes, microspheres, or the like). As will be understood by those of skill in the art, particles or molecules mixed with plasmid so as to "condense" the DNA molecule may also be employed.

Antisense nucleic acids are DNA or RNA molecules that are complementary to at least a portion of a specific mRNA molecule (see, e.g., Weintraub, Scientific American, 262:40, 1990) or any other nucleic acid sequence. In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause deleterious effects than larger molecules when introduced into the target cell. The use of antisense methods to inhibit the in vitro translation of genes is well known in the art (see, e.g., Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1(3):277-281, 1991; Helene, C., Anticancer Drug Design, 6(6):569, 1991). Accordingly, electroporation of nucleic acids useful for triplex formation is also contemplated as within the scope of the present invention.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that only mRNAs with particular sequences are inactivated because ribosomes are sequence-specific.

There are two basic types of ribozymes namely, tetrahymena-type (Hasselhoff, Nature, 334:585, 1988) and "hammerhead"-type. Tetrahymena-type ribozymes recognize sequences which are four bases in length, while hammerhead-type ribozymes recognize base sequences in the range of 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides methods of gene therapy for the treatment of cell proliferative or immunologic disorders mediated by a particular gene or absence thereof. The term "cell proliferative disorder" denotes malignant as well as non-malignant cell populations which often appear to differ from the surrounding tissue both morphologically and genotypically. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA, for example.

The polynucleotide sequences of the invention are DNA or RNA sequences having a therapeutic effect after being taken up by a cell. Nucleic acids contemplated for use in the practice of the present invention can be double stranded DNA (e.g., plasmid, cosmid, phage, viral, YACS, BACS, other artificial chromosomes, and the like) or single stranded DNA or RNA. The nucleic acids may be uncomplexed (i.e., "naked") or complexed (e.g., with chemical agents such as lipids (e.g., cationic), dendrimers, or other polyplexes that facilitate DNA penetration into tissues and through cell membranes, and the like). The DNA may also be encapsulated or formulated with protein complexes.

Examples of polynucleotides that are themselves therapeutic are anti-sense DNA and RNA; DNA coding for an anti-sense RNA; or DNA coding for tRNA or rRNA to replace defective or deficient endogenous molecules, and the like. The polynucleotides of the invention can also code for therapeutic polypeptides. As used herein, "polypeptide" is understood to be any translation product of a polynucleotide regardless of size, and whether glycosylated or otherwise modified, or not. Therapeutic polypeptides contemplated for use in the practice of the present invention include, as a primary example, those polypeptides that can compensate for defective or deficient species in an animal, or those that act through toxic effects to limit or remove harmful cells from the body.

Also included are polynucleotides which encode metabolic enzymes and proteins, such as blood coagulation compounds (e.g., Factor VII, VIII or IX), and the like.

In accordance with another embodiment of the present invention, there are provided methods for inducing an immune response in a subject. Invention methods of this embodiment comprise applying a pulsed electric field to dermis and underlying muscle cells of the subject substantially contemporaneously with the application of an immune response-inducing agent to the dermis and/or muscle cells, such that the immune response-inducing agent is introduced into the cells thereby inducing in the subject an immune response. As used herein, "immune response-inducing agent" means any agent, which upon introduction into the dermis and/or muscle cells of a subject, results in an immune response, whether such response be a cellular response, humoral response, or both. Immune response-inducing agents contemplated for use in the practice of the present invention include expressible nucleic acids, and polypeptides.

Expressible DNA and mRNA can be delivered to cells to form therein a polypeptide translation product. If the nucleic acids are operatively associated with the proper regulatory sequences, enhanced synthesis of the encoded protein is achievable. DNA or RNA encoded polypeptides contemplated for use in the practice of the present invention include immunizing polypeptides, pathogen-derived proteins, blood coagulation factors, peptide hormones, and the like. Peptide hormones include, for example, calcitonin (CT), parathyroid hormone (PTH), erythropoietin (Epo), insulin, cytokines, growth hormone, growth factors, and the like. Lymphokines contemplated for use in the practice of the present invention include tumor necrosis factor, interleukins 1, 2, and 3, lymphotoxin, macrophage activating factor, migration inhibition factor, colony stimulating factor, alpha-interferon, beta-interferon, gamma-interferon and subtypes thereof. Blood coagulation factors contemplated for use in the practice of the present invention include Factor VIII or Factor IX.

When the DNA or mRNA delivered to the cells codes for an immunizing peptide, invention methods can be applied to achieve improved and more effective immunity against infectious agents, including bacteria, intracellular viruses, tumor cells, and the like. Therapeutic polynucleotides used with the invention can also code for immunity-conferring polypeptides, which can act as endogenous immunogens (i.e., antigen-containing polypeptides) to provoke a humoral immune response, a cellular immune response-inducing agent response, or both. Methods for inducing such responses and targeting specific cells for specific responses are described, for example, in U.S. Pat. No. 5,589,466. The polynucleotides employed in accordance with the present invention can also code for an antibody. In this regard, the term "antibody" encompasses whole immunoglobulin of any class, chimeric antibodies and hybrid antibodies with dual or multiple antigen or epitope specificities, and fragments, such as F(ab).sub.2, Fab', Fab, and the like, including hybrid fragments thereof. Also included within the meaning of "antibody" are conjugates of such fragments, and so-called antigen binding proteins (single chain antibodies) as described, for example, in U.S. Pat. No. 4,704,692, hereby incorporated by reference herein in its entirety.

Thus, an isolated polynucleotide coding for variable regions of an antibody can be introduced, in accordance with the present invention methods, to enable the treated subject to produce antibody in situ. For illustrative methodology relating to obtaining antibody-encoding polynucleotides, see Ward et al. Nature, 341:544-546 (1989); Gillies et al., Biotechnol. 7:799-804 (1989). The antibody in turn exerts a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby ameliorating or preventing pathological conditions associated with an immune response, (e.g., in the context of an autoimmune disease such as lupus and the like).

It is presently preferred that polynucleotide sequences used in the practice of the present invention code for therapeutic or immunogenic polypeptides. These polynucleotide sequences may be used in association with other polynucleotide sequences coding for regulatory proteins that control the expression of the therapeutic or immunogenic polypeptides. The regulatory protein(s) so employed can act in any number of regulatory manners known to those of skill in the art, such as by binding to DNA so as to regulate its transcription, by binding to messenger RNA to increase or decrease its stability or translation efficiency, and the like.

The polynucleotide material delivered to the cells in vivo can take any number of forms, and the present invention is not limited to any particular polynucleotide coding for any particular polypeptide. Plasmids containing genes coding for a large number of physiologically active peptides and antigens or immunogens are contemplated for use in the practice of the present invention and can be readily obtained by those of skill in the art.

Various viral vectors can also be utilized in the practice of the present invention and include adenovirus, herpes virus, vaccinia, RNA virus, and the like. It is presently preferred that the virus be an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV), or the like can be used. A number of additional retroviral vectors can incorporate multiple genes. All of these vectors can transfer or incorporate a gene for a selectable marker so that transduced cells can be identified. In other embodiments, the vector can comprise a linear nucleic acid construct containing only a promoter and a gene sequence to be expressed in the cell following introduction by methods of the invention apparatus.

Therapeutic peptides or polypeptides may also be included in the therapeutic method of the invention. For example, immunomodulatory agents and other biological response modifiers can be administered for incorporation by a cell. As used herein, the term "biological response modifiers" encompasses substances which are involved in modifying the immune response. Examples of immune response modifiers include such compounds as lymphokines, and the like. Lymphokines include, for example, tumor necrosis factor, various interleukins e.g., for example IL-1, 2, and 3, lymphotoxin, macrophage activating factor, migration inhibition factor, colony stimulating factor, alpha-interferon, beta-interferon, gamma-interferon and their subtypes.

In accordance with another embodiment of the present invention, there are provided electrode kits for use in conjunction with electroporation therapy, each kit containing the components of the electrodes described herein. For example, in one aspect, there is provided an electrode kit comprising a ring electrode system including a ring electrode assembly wherein said assembly has a central elongate injection needle, optionally comprising one or more holes disposed along its length and proximal to the needle tip, wherein the holes are in fluid communication with the hollow interior of the injection needle, said elongate injection needle having a distal electrically conductive portion thereof. Further, such electrode kit can be equipped with any of various ring electrode designs and dimensions, including those ring electrodes compatible with use on either human skin or pelt covered animals.

Example I Rabbit Study to Show Focus of Electroporation to Tissue

In this example, the efficacy of a ring electrode system for electroporative intramuscular delivery was demonstrated using expression of Green Fluorescing Protein (GFP) plasmid-DNA in rabbit quadriceps muscle.

Specifically, adult New Zealand white male rabbits (n=2) were treated in the quadriceps muscles with injections of 200 μL (microliter) of plasmid-DNA encoding the GFP protein and a needle penetration depth of 1.6 cm using the elongate electrode as the delivery needle. The experiment was divided between ring electrode systems incorporating alternate embodiments, specifically:

The first rabbit received 4 injections (one each into the upper and lower parts of the left and right quadriceps muscles) using either a 22 g or a 23 g injection needle for injection and as the elongate electrode. One of the four injections used two parallel uninsulated 22 g needles in the Elgen device (no ring electrode). In the remaining three injections, the ring electrode was an ovoid copper electrode having a surface area of 10 cm$^2$. The upper section of the delivery needle electrode was coated with a ultraviolet-cured epoxy (Loctite 4304) leaving approximately 0.8-1.0 cm exposed metal on the distal tip of the needle for electrode conduction in the biological tissue to focus electric current only in the targeted section of the muscle. An electrode lead was attached to a sufficient section of proximal needle at the base of the syringe needle to permit electrical communication with the electric pulse generator.

The second rabbit received 4 injections, one each into the upper and lower parts of the right and left quadriceps muscle using either a 22 g or 23 g injection needle. Insulation was placed on the injection needle using a 22 g introducer sheath leaving approximately 0.8 cm exposed metal on the distal tip of the needle for electrode conduction in the biological tissue, to focus electric current only in the targeted section of the muscle. The base of the needle was also connected to the pulse generator as in the first rabbit test. The ring electrode was an ovoid copper ring electrode having a surface area of 20 cm$^2$. The experimental setup was as shown in Table III.

TABLE III

| Rabbit | Delivery Site Left Q (upper/lower) | Delivery Site Right Q (upper/lower) | Delivery electrode size | Insulation type | Area of uninsulated delivery electrode | Ring electrode area | Pulse voltage (V) |
|---|---|---|---|---|---|---|---|
| 1 | U | | 23 g | 22 g sheath | 8 mm | 10 cm² | 110 |
| 1 | L | | 23 g | 22 g sheath | 8 mm | 10 cm² | 54 |
| 1 | | U | 22 g | epoxy | 8 mm | 10 cm² | 54 |
| 1 | | L | Two 22 g | N/A | | n/a | 54 |
| 2 | U | | 23 g | 22 g sheath | 8 mm | 20 cm² | 54 |
| 2 | L | | 23 g | 22 g sheath | 8 mm | 20 cm² | 106 |
| 2 | | U | 22 g | epoxy | 8 mm | 20 cm² | 106 |
| 2 | | L | One 23 g | N/A | | n/a | 106 |

Q equals quadriceps muscle

For carrying out the electroporation, an Inovio Elgen model 1000 generator (Genetronics, Inc., San Diego, Calif.) was used and standard electrode gel (Lectron II conductivity gel) was applied to the surface of the ring electrode in contact with the test animal skin surface. The Elgen pulse generator was set up to deliver two 60 msec duration pulses separated by a 250 msec interval (4 Hz) between the needle and the ring electrodes. The pulse amplitude was governed by either approx. 400 mA max current, or 50 V or 100 V maximum voltage. The current and voltage achieved in the tissue were measured and recorded, and the apparent tissue impedances were calculated as disclosed in Table IV.

TABLE IV

| | Volts | I (mA) | R (Ω) |
|---|---|---|---|
| Data 100Ω Resistor Control | 44 | 382 | 114 |
| | 44 | 381 | 115 |
| Data 1 - 1 LU - 10 cm2, SH, 110 V | 105 | 382 | 273 |
| | 110 | 382 | 286 |
| Data 2 - 1 LL - 10 cm2, SH, 54 V | 53 | 140 | 380 |
| | 53 | 151 | 351 |
| Data 3 - 1 RU - 10 cm2, UV, 54 V | 53 | 97 | 548 |
| | 53 | 112 | 474 |
| Data 4 - 1 RL - 2 Ndls, CTRL, 54 V | 51 | 385 | 133 |
| | 50 | 386 | 128 |
| Data 5 - 612 LU - 20 cm2, SH, 54 V | 53 | 153 | 347 |
| | 53 | 167 | 318 |
| Data 6 - 612 LL - 20 cm2, SH, 106 V | 92 | 386 | 237 |
| | 90 | 386 | 231 |
| Data 7 - 612 RU - 20 cm2, UV, 106 V | 98 | 385 | 254 |
| | 95 | 385 | 245 |
| Data 8 - 612 RL - 20 cm2, CTRL, 106 V | 78 | 387 | 200 |
| | 76 | 385 | 198 | key: LU = Left Upper Quad Muscle; LL = Left Lower Quad Muscle; RU = Right Upper Quad Muscle; RL = Right Lower Quad Muscle; SH = Sheath shielded; UV = UV epoxy shielded; 2 Needles = Standard ELGEN; 10 cm2 = Small electrode plate; 20 cm2 = Large electrode plate Upon calculating the pulsing parameters one of skill in the art will recognize the variation in the actual voltages sent in the pulses versus the value set on the instrument dial, for example, 53 V as opposed to 54 V. This variation is due to the specific sensitivities of the electronics of the instrument. In any event the average of the impedances of the tissue during the electroporation were calculated from output data of the electroporation as shown in Table IV. The averages calculated are close to true values given the pulse shape, i.e., a monopolar square wave (not shown), was fairly flat with respect to both current and voltage drop and only a slight decrease in impedance throughout each pulse.

Of the various observations respecting the use of the ring electrode system of the present invention one phenomenon is clear, namely that the larger the ring electrode surface area, the lower the apparent tissue impedance while other parameters were as follows: higher voltage is associated with lower apparent tissue impedance, insulation of the needle electrode increases apparent tissue impedance, epoxy resin insulation had a higher impedance than plastic sheathing, and the ring electrode system impedance indicated a higher apparent tissue impedance than for the bare needle electrode system of the Elgen device.

The Elgen device with two needles of approximately 2 cm in length and separated by about 0.4 cm results in an apparent tissue impedance of between 100 and 200 ohms. The single needle with ring configuration using a 23 gauge needle of 1 cm exposed tip and a surface ring of between 20 and 40 cm² results in an apparent tissue impedance of between 200 and 350 ohms, as shown by the data set 5 through 8 in Table IV. The significance of this is that apparent tissue impedance using the invention apparatus versus using a dual inserted elongate electrode of the Elgen device, or other similar dual insertable electrode array, is that the observed impedance is only slightly higher using the ring electrode system. Thus, all things being equal between a dual needle system and the invention ring electrode apparatus, the invention apparatus uniquely provides for a differential in current density sufficient for poration of the cells allowing for focusing of pulse energy to only a focused area of tissue.

Turning now to GFP gene expression results, the test rabbits were anesthetized with intravenous administration of Ketamine/Zylazine during the electroporation procedure, allowed to incubate for approximately three days to permit GFP gene expression, then euthanized with intravenous injection of Pentorbarbital after which the quadriceps muscle was removed from the animal and sliced, examined and photographed under fluoroscopic and/or visible lighting. In each muscle tested, GFP expression was clearly present. The needle track was clearly visible in most images, showing good co-localization of the injected material and the electroporation procedure. For example, the lowest voltage (53 Volts) gave good GFP expression with current measured at 100 mA. In contrast, 50 to 100 Volt electroporation settings with the dual needle electrode Elgen device typically delivered between 400 mA and 1 Amp or more. Therefore, in confirming the present invention, less energy is required (low current, high impedance) as a result of insulating the proximate portion of the elongate electrode and placing a large counter electrode on the surface of the skin causing the electroporative energy to be focused near the uninsulated portion of the elongate needle in deep muscle tissue, rather than near and between two needle electrodes piercing the skin and underlying muscle. In other words, electroporation is focused away from the skin such that sensation of electricity should be minimal at the skin due to the substantially lower current density at the skin. In FIGS. 9A to F are shown examples as discussed above of the results seen in all of the GFP expression experiments examined. FIGS. 9B and F show a fluorescence field and a mixed fluorescence and visible light. As is clearly visible, the electroporation has been localized to the deep muscle tissue.

Sensitivity.

In still further embodiments, as the surface area of the ring electrode increases, sensation in the surface tissues should decrease. Based on the previous discussion on current densities, the ring electrode can be anywhere between 5 and 1000 times the surface area of the elongate electrode within preferred embodiments. Therefore, since pain is primarily thought to be a function of current density, the sensation at the ring electrode is likely significantly reduced compared to the sensation that an elongate electrode would cause.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An electroporation system for delivering a molecule into cells of a focused area of tissue by providing a differential current density to a mammal, the electroporation system comprising:
   a) a geometric planar ring electrode with a multiplicity of electrically conductive projections thereon, wherein said geometric planar ring electrode is electrically isolatable into two electrically conductive halves;
   b) a tissue-piercing elongate electrode having a proximal and a distal end, said tissue-piercing elongate electrode having a nonconductive portion and a conductive portion, said nonconductive portion lying between said proximal end and between about 2.5 cm and at least 0.1 cm from the distal end, said nonconductive portion comprising either an insulator coating on said tissue-piercing elongate electrode or a nonconductive material;
   c) a housing associated with said geometric planar ring electrode and tissue-piercing elongate electrode;
   d) a charging unit for charging a capacitor; and
   e) a computer in electrical communication with said charging unit, said computer comprising software capable of performing programming functions for said system;
   f) wherein the tissue-piercing elongate electrode defines a plurality of apertures that are positioned on the conductive portion of the tissue piercing-elongate electrode such that there are between approximately 10 and approximately 100 apertures per centimeter of length of the conductive portion, and the apertures are spaced around an entire circumference of the conductive portion and have a diameter in a range of 30 microns to 80 microns, wherein the aperture positioning, spacing, and diameters are configured to provide even distribution of an injection fluid over an entire length of the conductive portion.

2. The electroporation system of claim 1, wherein said geometric planar ring electrode is of a geometric shape selected from the group consisting of donut, oval, donut circle, isosceles triangle donut, equilateral triangle donut, a square donut, rectangular donut, a pentagonal donut and a hexagonal donut.

3. The electroporation system of claim 2, wherein the multiplicity of electrically conductive projections have respective tips that collectively define a total tip surface area for conducting current proportional to a surface area of the conductive portion of said tissue-piercing elongate electrode, wherein a surface area ratio of the total tip surface area and the surface area of the conductive portion is selected from the group consisting of 5:1, 10:1, 100:1, and 1000:1.

4. The electroporation system of claim 1, wherein said tissue-piercing elongate electrode is tubular and capable of channeling a fluid medium from said proximal end to said distal end, said proximal end being in fluid communication with a reservoir, and the length of said conductive portion is between about 1.0 and 1.5 cm of a distal portion of said tissue-piercing elongate electrode.

5. The electroporation system of claim 1, wherein said apertures have a diameter selected from the group consisting of 80 microns, 70 microns, 60 microns, 50 microns, 40 microns, and 30 microns.

6. The electroporation system of claim 1, wherein the housing further comprises an actuator; and wherein said actuator is selected from a motor, a mechanically driven actuator and an animatedly driven actuator.

7. The electroporation system of claim 6, wherein:
the distal end of the tissue-piercing elongate electrode defines a tip that does not have an aperture, such that all of the plurality of apertures are located around the circumference of the conductive portion; and
said actuator is capable of driving both:
the tissue-piercing elongate electrode in a linear motion distally into the tissue relative to the geometric planar ring electrode; and
a fluid medium from a reservoir through a lumen in said tissue-piercing elongate electrode to and out the plurality of apertures in the conductive portion at a pressure substantially equivalent to a pressure necessary to expel the fluid medium from a hypodermic needle having 1) a lumen with a diameter equivalent to a diameter of the lumen of the tissue-piercing elongate electrode, and 2) a single aperture, wherein the single aperture is located at a distal tip of the hypodermic needle.

8. The electroporation system of claim 7, wherein said actuator creates a pressure that allows said fluid medium to pass through each aperture at equivalent flow dynamics.

9. The electroporation system of claim 1, wherein said tissue-piercing elongate electrode is a negative electrode.

10. The electroporation system of claim 1, wherein each aperture defined by the tissue-piercing elongate electrode is positioned to provide radial delivery of an injection substance.

11. A variable current density electrode system for in vivo electroporation, the variable current density electrode comprising:
a) a geometric planar ring electrode with a multiplicity of electrically conductive projections thereon, wherein said ring electrode is electrically isolatable into two electrically conductive halves;
b) an elongate needle electrode that is partially insulated and includes a conductive portion along a portion of a distal end of the elongate needle electrode; and
c) a surface area ratio between said geometric planar ring electrode and said elongate needle electrode selected from the group consisting of a range between 1000:1 and 5:1;
characterized in that when said electrode system is activated by providing an electric pulse in a body tissue, electric current density in said body tissue at or near said elongate needle electrode is higher than current density in said body tissue at or near said geometric planar ring electrode;
d) wherein the elongate needle electrode defines a plurality of apertures that are positioned on the conductive portion such that there are between approximately 10 and approximately 100 apertures per centimeter of length of the conductive portion, and the apertures are spaced around an entire circumference of the conductive portion and have a diameter in a range of 30 microns to 80 microns, wherein the aperture positioning, spacing, and diameters are configured to provide even distribution of an injection fluid over an entire length of the conductive portion.

12. The variable current density electrode system of claim 11, wherein said geometric planar ring electrode has a surface area of between 1 cm$^2$ and 100 cm$^2$.

13. The variable current density electrode system of claim 11, wherein the length of the conductive portion is between 0.01 cm and 2.5 cm.

14. The variable current density electrode system of claim 13, wherein said conductive portion has an electrically conductive surface area between 0.05 cm$^2$ and 1.00 cm$^2$.

15. The variable current density electrode system of claim 11, wherein said elongate needle electrode includes insulation that extends between a proximal end of the elongate needle electrode and to within about 0.1 cm to 2.5 cm of the distal end of the elongate needle electrode.

16. The variable current density electrode system of claim 15, wherein the insulation of said elongate needle electrode is selected from group consisting of plastic, paralene, polytetrafluoroethylene and epoxy.

17. The variable current density electrode system of claim 11, wherein said geometric planar ring electrode is charged with a positive charge and wherein said elongate needle electrode is charged with a negative charge.

18. The variable current density electrode system of claim 17, wherein said negative charged elongate needle electrode results in negligible shedding of metal ions from said elongate needle electrode into said body tissue upon discharge of an electroporative pulse into said tissue.

19. The variable current density electrode system of claim 11, wherein said geometric planar ring electrode has a geometric shape selected from the group consisting of donut, oval, donut circle, isosceles triangle donut, equilateral triangle donut, a square donut, rectangular donut, a pentagonal donut and a hexagonal donut.

20. The variable current density electrode system of claim 11, wherein said elongate needle electrode is tubular and capable of channeling a fluid medium from a reservoir, and the length of said conductive portion is between about 1.0 cm and 1.5 cm of a distal portion of said elongate needle electrode.

21. The variable current density electrode system of claim 11, wherein said apertures have a diameter selected from the group consisting of 80 microns, 70 microns, 60 microns, 50 microns, 40 microns, and 30 microns.

22. An electroporation system for delivering a molecule into cells of a focused area of tissue by providing a differential current density to a mammal, the electroporation system comprising:
a) a geometric planar ring electrode with a multiplicity of electrically conductive projections thereon, wherein said ring electrode is electrically isolatable into two electrically conductive halves;
b) an elongate electrode having a proximal end and a distal end, the distal end defining a tip for piercing the tissue, said elongate electrode having a nonconductive portion and a conductive portion, said nonconductive portion lying between said proximal end and between about 2.5 cm and at least 0.1 cm from the distal end, said nonconductive portion comprising either an insulator coating on said elongate electrode or a nonconductive material;
c) a housing associated with said geometric planar ring electrode and said elongate electrode;
d) a charging unit for charging a capacitor; and
e) a computer in electrical communication with said charging unit, said computer comprising software capable of performing programming functions for said system;
f) wherein the elongate electrode defines a plurality of apertures that are spaced around an entire circumference of the conductive portion of the tissue piercing elongate electrode such that there are between approximately 10 and approximately 100 apertures per centimeter of length of the conductive portion, the apertures have a diameter in a range of 30 microns to 80 microns, and the tip of the elongate electrode does not include an aperture, such that all of the plurality of apertures are located around the circumference of the conductive portion, wherein the aperture spacing and diameters are configured to provide even distribution of an injection fluid over an entire length of the conductive portion.

23. The electroporation system of claim 22, further comprising:
a first lead at a distal portion of the elongate electrode; and
a second lead disposed on the elongate electrode and spaced proximally from the first lead, wherein the second lead is electrically isolated from the first lead, and the first and second leads are in electrical communication with the computer,
wherein the first and second leads are configured to 1) deliver electric pulses from the capacitor to the tissue, 2) sense parameters of the pulses, and 3) transmit the sensed parameters to the computer for calculating respective impedances of the tissue in which the first and second leads are advanced.

24. The electroporation system of claim 23, wherein the parameters include voltage and resistance.

25. The electroporation system of claim 23, wherein:
the housing includes an actuator that is in fluid communication with a reservoir of the injection fluid and with a lumen of the elongate electrode, and the lumen is in fluid communication with the plurality of apertures;
the computer is configured to identify, based on the sensed parameters, when the first lead advances distally beyond an interface between adipose tissue and muscle tissue, and
the computer is further configured to subsequently actuate the actuator to thereby drive the injection fluid through the plurality of apertures, thereby providing the even distribution of the injection fluid over the entire length of the conductive portion into the focused tissue, as the tip further advances distally into the muscle tissue.

26. The electroporation system of claim 25, wherein the actuator is further configured to drive the elongate electrode in a linear motion distally into the tissue relative to the geometric planar ring electrode.

* * * * *